United States Patent

Sawada et al.

[11] Patent Number: 5,849,417
[45] Date of Patent: Dec. 15, 1998

[54] TITANIUM IMPLANTATION MATERIALS FOR THE LIVING BODY

[75] Inventors: Susumu Sawada, Tokyo; Tateo Ohhashi, Kitaibaraki; Ichiro Sawamura, Kitaibaraki; Toshiaki Shimada, Kitaibaraki, all of Japan

[73] Assignee: Japan Energy Corporation, Tokyo, Japan

[21] Appl. No.: 526,612

[22] Filed: Sep. 11, 1995

[30] Foreign Application Priority Data

| Sep. 12, 1994 | [JP] | Japan | 6-242424 |
| Oct. 11, 1994 | [JP] | Japan | 6-270156 |
| Feb. 8, 1995 | [JP] | Japan | 7-042604 |
| Feb. 8, 1995 | [JP] | Japan | 7-042605 |
| Aug. 15, 1995 | [JP] | Japan | 7-228634 |

[51] Int. Cl.$^6$ .................................................. B32B 9/00
[52] U.S. Cl. ..................... 428/472.1; 148/421; 433/207
[58] Field of Search .................... 420/417; 148/421; 428/472.1; 433/20, 207; 623/13

[56] References Cited

U.S. PATENT DOCUMENTS

| 3,482,968 | 12/1969 | Hunter | 148/421 |
| 4,886,559 | 12/1989 | Shindo et al. | 420/417 |
| 5,141,565 | 8/1992 | Kramer et al. | 148/421 |
| 5,152,993 | 10/1992 | Bjursten et al. | |
| 5,196,916 | 3/1993 | Ishigami et al. | 420/417 |
| 5,354,390 | 10/1994 | Haszmann et al. | 148/518 |
| 5,514,332 | 5/1996 | Horiya et al. | 420/417 |

FOREIGN PATENT DOCUMENTS 0 248 338  12/1987  European Pat. Off. ............... 420/417

OTHER PUBLICATIONS

Publication—Susumu Sugita et al.; *An Experimental Study of Titanium and Titanium Alloy as Implant for Wire*; 1989.
Publication—Susumu Sugita; *An Experimental Study of Titanium and Titanium Alloy as the Surgical Wire*; 1991.

*Primary Examiner*—John Sheehan
*Attorney, Agent, or Firm*—Panitch Schwarze Jacobs & Nadel, P.C.

[57] ABSTRACT

Implantation materials for the living body comprising: 10 to 4000 ppm of gaseous ingredients combined, mainly composed of oxygen; up to 100 ppm of ingredients other than the gaseous ingredients such as iron; and the balance titanium. An oxide film is formed on the surface, where necessary, by anodizing or the like. Titanium fixation wires for implanting in the living body composing: up to 300 ppm oxygen, up to 50 ppm hydrogen, up to 200 ppm nitrogen, and up to 400 ppm carbon, all as gaseous ingredients; up to 100 ppm of ingredients other than the gaseous ingredients such as iron; and the balance titanium. For applications where strength is the primary consideration, the wires comprise: from more than 100 to 1000 ppm of iron; up to 250 ppm oxygen, up to 50 ppm hydrogen, up to 170 ppm nitrogen, and up to 400 ppm carbon, all as gaseous ingredients; up to 100 ppm of iron and ingredients other than the gaseous ingredients; and the balance titanium.

37 Claims, 31 Drawing Sheets

Change in elongation with oxygen content

Typical anodic polarization curve of UP-Ti, HP-Ti, CP-Ti and SUS316L

Typical anodic polarization curve of anodic oxidated UP-Ti, HP-Ti, CP-Ti and passivated SUS316L (SSTM F-86)

Change in elongation with oxygen content

Change in elongation with carbon content

Change in elongation with nitrogen content

Change in elongation with hydrogen content

Change in gap with oxygen content

Change in gap with carbon content

Change in gap with nitrogen content

Change in gap with hydrogen content

Type A

Type B

Type C

Patterns of breaks classified by types

Change in elongation with iron content

Change in elongation with oxygen content

Change in elongation with nitrogen content

Change in elongation with carbon content

Change in elongation with hydrogen content

Changes in proof stress and tensile strength with iron content

Changes in proof stress and tensile strength with oxygen content

Changes in proof stress and tensile strength with nitrogen content

Changes in proof stress and tensile strength with carbon content

Changes in proof stress and tensile strength with hydrogen content

Change in gap with iron content

Change in gap with oxygen content

Change in gap with nitrogen content

Change in gap with carbon content

Change in gap with hydrogen content

TITANIUM IMPLANTATION MATERIALS FOR THE LIVING BODY

FIELD OF THE INVENTION

This invention relates to titanium implantation materials for the living body which are excellent in the corrosion resistance in the living body. More particularly, this invention relates to implantation materials useful in dental, orthopedic and related applications because of their adequate strength as bone replacements or reinforcements, excellent biocompatibility and corrosion resistance in vivo, and ability to enhance the connective strength with bone tissues. This invention also relates to excellent titanium surgical wires or fixation wires for the living body, e.g. for binding of human bones together which permit to bind them easily and firmly during surgical operation, with high degrees of safety in the living body.

BACKGROUND OF THE INVENTION

In recent years it has been in practice in the medical fields, especially of orthopedic and oral surgeries, to implant or embed artificial bones, artificial roots of teeth, and other objects in the body. In cases of a bone fracture, in particular, it is common that an artificial bone is inserted or grafted into the fractured part or an insert is used to reinforce or fix the bone until the latter is restored. Also, vertebral operations and the like involve transplantation of bones.

Stainless steels and chromium-cobalt based alloys are often used in making those artificial bones, joint materials, and their reinforcements. However, stainless steels and chromium-cobalt based alloys contain elements noxious to the human body. Reports of malignant tumors found as complications of artificial joint replacements are not a few. Thus, the dissolving out of toxic metal ions into the body has recently presented a problem.

Although stainless steels are generally known as corrosion-resistant materials, they are rather easily broken by pitting, corrosion fatigue, sress corrosion cracking and the like in the living body which is a highly corrosive environment. The stainless steel itself is possibly damaged during the course of a surgical operation or otherwise in use which damage can lead to partial destruction of the corrosion resistant film (passivated film) on the surface. Should this happen in the air, the passivated film would be rapidly regenerated, but in the body where the partial pressure of oxygen is low, the film-free surface is kept to be exposed for long with a possibility of the metal ions of nickel, a major additional element of the stainless steel, etc. dissolving out. There are reports that metallic nickel itself is toxic as an allergy-inducing or cancer-causing substance.

As other metallic objects to be implanted in the body, metallic wires are in use for the fixation or reinforcement of bones together, or bone and artificial bone, or of grafted bones. Stainless steel wires have been widely used again for these purposes because of their high strength. Stainless steel wires, however, can undergo galvanic corrosion with the metallic artificial bones referred to above, with a danger of the metallic ions dissolving out even more easily.

In view of these and other problems presented in the art, there is a need for implantation materials for the living body which possess the following properties:

(1) Biocompatibility
  No cytotoxicity or toxicity in itself
  No dissolution out in the form of metallic ions
  Good adaptability to the tissues in the body
  Neither carcinogenic nor antigenic
  Causing no metabolic disorder
  Causing no blood clotting or hemolysis
  No biodegradation or decomposition
  No adsorptivity or precipitate production
(2) Mechanical properties
  Adequate static (tensile, compressive, bending, and shear) strengths and ductility
  Sufficient fatigue strength
  Excellent workability The afore-described problems in the art have developed a tendency to avoid the use of toxic metals or alloys containing such toxic metals.

Thus, titanium materials have attracted increasing attention as more corrosion-resistant and lighter substitutes for stainless steels and chromium-cobalt alloys.

Titanium materials are roughly divided into two; pure titanium and titanium alloys. Pure titanium varies in strength with its oxygen content. JIS (Japanese Industrial Standards) classify pure titanium into three, Grade 1 to Grade 3, in the order of increasing oxygen content.

On the other hand, with regard to titanium alloys, the beta phase comes to be present up to room temperature as the contents of beta stabilizers such as V, Mo, Fe, and Cr in the alloys increase. Titanium alloys are classified into three types, $\alpha$ type, $\alpha$-$\beta$ type, and $\beta$ type, depending on whether there is this beta phase. Of those titanium alloys, Ti-6Al-4V is popular for medical applications. It is specified as an implantation material for surgical uses in the standards of ASTM and ISO. However, this alloy contains vanadium that is known to be strongly cytotoxic when used singly, and the danger of this alloy has been pointed out by some researchers. For this reason the development of V-free titanium alloys for use in the living body is under way.

It is a generally accepted belief that titanium is not particularly questionable in respect of cytotoxicity. However, if an artificial bone and a bone reinforcement or a fixation wire are used together in the same region in vivo, their contacting parts are both kept to be soaked in the body fluid, with much possibility of undergoing electrochemical corrosion. This is particularly true with the use of dissimilar materials, e.g., titanium and stainless steel. It thus seems advisable that, when implantation materials of pure titanium or a titanium alloy are employed for the living body as artificial bones or the like, the same kinds of titanium materials be used.

Titanium materials are said inferior to stainless steels in mechanical strength and elongation. At the present time, a final conclusion is yet to be drawn out of whether titanium materials, even the pure titanium specified in the standards of ASTM (and JIS), are suited as implantation materials for the living body.

A major problem that arises from the use of titanium materials as fixation wires in the living body is the binding force they exert. When a wire is used in fixing a bone in place, the fixing is commonly done by twisting the wire. It is deemed essential that the binding with twists fasten the wire fitly around the object lest it loosen later and that the wire should not break during and after binding.

To meet such needs, as pure titanium implantation materials, two types of pure titanium that meet JIS requirements have already been proposed (Japanese Patent Application Kokai Nos. 6-125978 (1994) and 5-23355 (1993)). Also, Grade 2 for JIS, with strength enhanced by an increase in the oxygen content, has been proposed, and there are reports on relatively good binding quality of the proposed materials.

It is true that the pure titanium conforming to the aforementioned JIS requirements (hereinafter called "CP titanium") has the advantages of good workability and greater corrosion resistance than other materials. However, when the passivated film formed on the titanium surface is not necessarily complete, there is the possibility of the metal dissolving out in the form of ions. It has been reported that a high concentration of titanium that has dissolved out can have deleterious effects upon the human body. This hazard cannot be ignored since the implants as bone replacements or reinforcements are used for long in the body. Moreover, even CP titanium contains certain amounts of metallic ingredients as impurities. These impurities tend to cause localized disturbances in the structure of the oxide film on the surface, leading to deterioration of the corrosion resistance.

In view of the above, an attempt has been made to increase the corrosion resistance by alloying. It aims at concentrating a highly corrosion-resistant element on the surface through initial dissolving-out. This means that the dissolution of a metal to a certain degree is prerequisite for the enhancement of corrosion resistance by alloying. This mechanism of corrosion resistance portends much delay in recovery of the alloy corrosion-resistant film when it is broken in the human body. At present, titanium alloy is not a fundamental solution yet of the afore-described problems.

When employed as a fixation wire, a wire of the pure titanium in conformity with JIS is likely to be broken upon several twists or be not coiled tightly around the object but be loosely wound and broken. CP titanium does not pose major problems such as cytotoxicity but it still leaves the above and other problems unsettled today.

Among other approaches, many are directed to improvements in binding method, including a proposal of mechanical fixing by caulking. The proposal cannot be regarded as a fully effective solution because it requires special tools for caulking in addition to varied surgical instruments and devices, and also requires certain skill, inevitably complicating the binding operation.

OBJECT OF THE INVENTION

An object of this invention is to provide an excellent material as implantation material for the living body having a combination of good strength and elongation and improved in vivo corrosion resistance.

Another object of this invention is to provide an excellent implantation materials which are quick to form a corrosion-resistant film and even if destroyed by deformation or the like, can be regenerated promptly.

A further object of this invention is to provide a fixation wire for the living body which can fasten the wire fitly around the object lest it loosen later and which the wire should not break during and after binding.

SUMMARY OF THE INVENTION

After intensive testing and research about the above-described problems, we have now found, through more exact and strict control of contents of ingredients contained in titanium than before, excellent materials as implantation materials for the living body having good workability and strength and improved in vivo corrosion resistance, the materials also being usable as fixation wires for use in the body without loosening or breaking. This discovery has now led to this invention.

CP titanium, as noted above, has had the shortcoming of not rapidly and fully forming a passivated film (oxide film). Under the invention, however, a striking improvement in corrosion resistance as an implantation material has now been achieved through further purification to minimize the contents of the elements that hamper the formation of a passivated film (oxide film). Thus, the present invention provides excellent implantation materials which are quick to form a corrosion-resistant film and, even if destroyed by deformation or the like, can be regenerated promptly.

To be more specific, this invention basically provides a titanium implantation material for the living body characterized in that the total amount of gaseous ingredients mainly composed of oxygen is controlled to 10 to 4000 ppm, and the upper limit of ingredients other than the gaseous ingredients such as iron is set to 100 ppm, the balance being titanium.

The term "gaseous ingredients" used herein means ingredients which is mainly composed of oxygen and which may include hydrogen, nitrogen and carbon. Carbon is removed as a gas such as CO, $CO_2$, etc. during the melting procedure such as vacuum arc melting or electron beam melting. For the reason, carbon was regarded as a kind of gas and was herein included in "gaseous ingredients" for convenience sake.

The term "ingredients other than gaseous ingredients" used herein means iron and other impurities possibly included in titanium material such as Ni, Cr, Mo, Sn, Al, Cu, Mn, Zr, Co, Na, K, U, Th etc.

This invention also provides a titanium implantation material for the living body characterized in that an oxide film is formed on the surface by anodizing, thermal oxidation, molten salt oxidation, or the like wherein the total amount of gaseous ingredients mainly composed of oxygen (excluding the oxygen contained in a surface oxide film) is controlled to 10 to 4000 ppm, and the upper limit of ingredients other than the gaseous ingredients such as iron is 100 ppm, the balance being titanium.

In the titanium implantation materials as defined above, preferably, the upper limits of the amounts of the gaseous ingredients contained are 50 ppm for hydrogen, 200 ppm for nitrogen, and 400 ppm for carbon.

Also in the titanium implantation materials as defined above, preferably, the material has a tensile strength (TS) of 175 MPa or more and an elongation (El) of 10% or more.

In another aspect, this invention provides a titanium fixation wire for implanting in the living body characterized in that, the upper limits of the amounts of the gaseous ingredients contained are 300 ppm, preferably 200 ppm, more preferably 100 ppm for oxygen, 50 ppm for hydrogen, 200 ppm for nitrogen, and 400 ppm for carbon; and the upper limit of the total amount of ingredients other than the gaseous ingredients such as iron is 100 ppm, the balance being titanium.

In the titanium fixation wire for implanting in the living body as defined above, the upper limit of the hydrogen content is preferably 30 ppm, more preferably 20 ppm; the upper limit of the nitrogen content is preferably 100 ppm, more preferably 50 ppm, even more preferably 20 ppm; the upper limit of the carbon content is preferably 200 ppm, more preferably 100 ppm, even more preferably 50 ppm; and the upper limit of the total amount of the ingredients other than the gaseous ingredients such as iron is preferably 50 ppm or more preferably 20 ppm.

Also in the titanium fixation wire for implanting in the living body as defined above, desirably, the average crystal grain diameter of the wire is 2 to 150 $\mu$m.

For applications where strength is the primary consideration, this invention also provides a titanium fixation wire for implanting in the living body characterized in that the iron content is more than 100 to 1000 ppm; the upper limits of the amounts of the gaseous ingredients contained are 250 ppm for oxygen, 50 ppm for hydrogen, 170 ppm for nitrogen, and 340 ppm for carbon; and the upper limit of the total amount of ingredients other than iron and said gaseous ingredients is 100 ppm, the balance being titanium wherein the iron content is preferably from more than 100 to 800 ppm and more preferably from more than 100 to 600 ppm; the upper limit of the oxygen content is preferably 200 ppm and more preferably 150 ppm; the upper limit of the hydrogen content is preferably 30 ppm and more preferably 20 ppm; the upper limit of the nitrogen content is preferably 100 ppm, more preferably 50 ppm, even more preferably 20 ppm; the upper limit of the carbon content is preferably 200 ppm, more preferably 100 ppm, even more preferably 50 ppm; and the upper limit of the total amount of ingredients other than iron and said gaseous ingredients is preferably 50 ppm and more preferably 20 ppm and further desirably, the average crystal grain diameter of the wire is 2 to 150 $\mu$m.

In the titanium fixation wires for implanting in the living body as defined above, desirably, the lower limit of oxygen content is may be 10 ppm.

In the titanium implantation materials as defined above, preferably, the material has a tensile strength (TS) of 175 MPa or more and an elongation (El) of 30% or more.

DETAILED DESCRIPTION OF THE INVENTION

Figure 1:
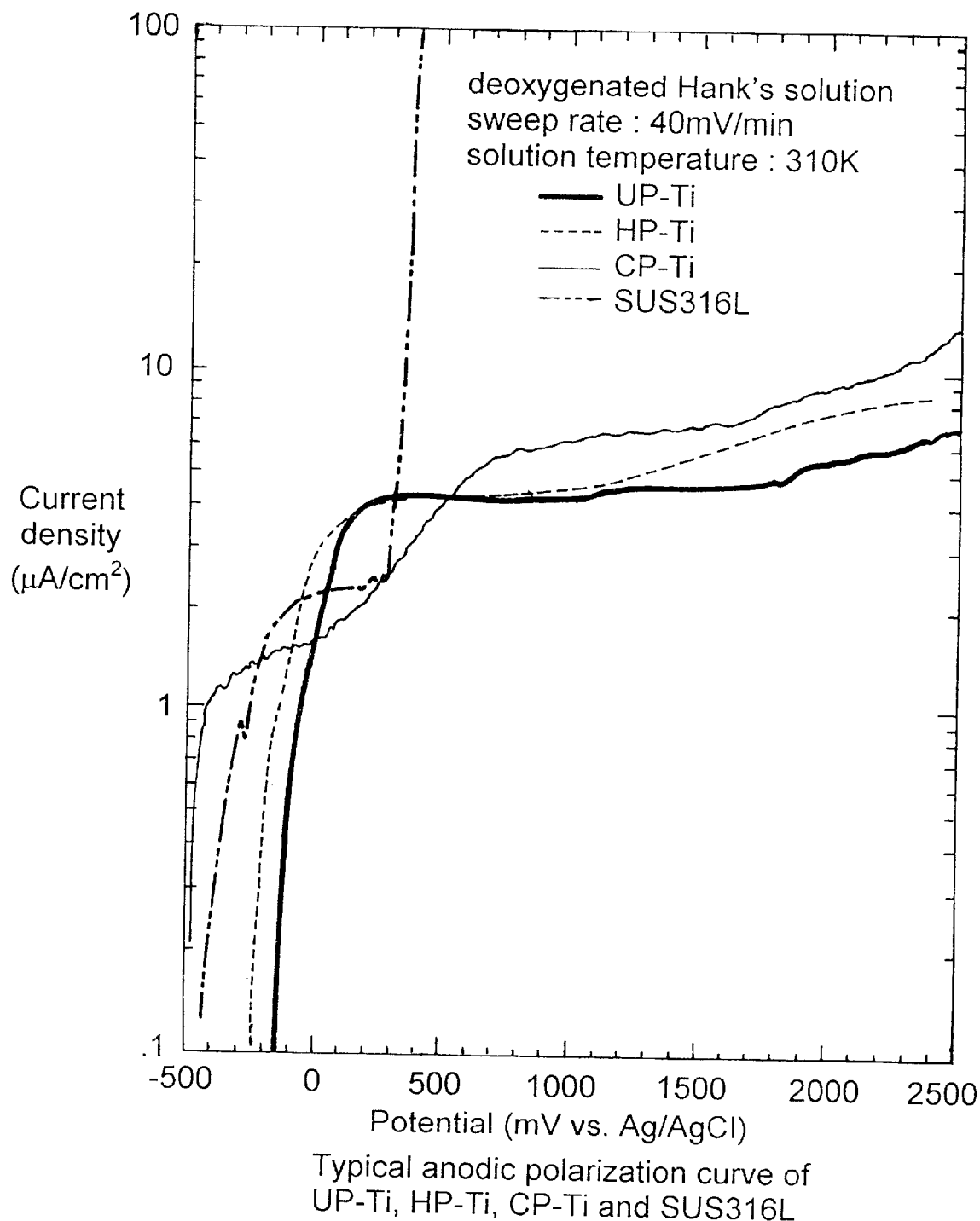
FIG. 1 is a graph showing anodic polarization curves of titanium and stainless steel specimens of Example 1 and Comparative Example 1 which had no passivated film formed on the surface.

This invention and its functions will now be described in detail.

First, the reasons for which the contents of oxygen and other elements in the titanium implantation materials for the living body according to this invention are limited within the specified ranges will be explained below.

Gaseous Ingredients

Oxygen (O)

In the present invention, the total amount of the gaseous ingredients, mainly oxygen, is specified to range from 10 to 4000 ppm. To form a passivated film (oxide film) rapidly, it is necessary to minimize the contents of alloying elements and impure elements in titanium, with an inevitable sacrifice of strength. As will be described later, the strength of titanium can be largely maintained through the adjustment of the oxygen content, while the enhancement of the strength can be controlled also with plastic working or heat treatment to produce a recrystallization texture.

The presence of oxygen in titanium does not affect the formation of a passivated film (oxide film), and the oxygen content is desirably at least 10 ppm. The strength is improved as the oxygen content increases.

On the surface of a titanium implantation material for the living body, an oxide film can be formed beforehand by anodizing, thermal oxidation, molten salt oxidation, or the like. The resulting uniform, dense oxide film markedly improves the corrosion resistance of the implantation material. The total content of gaseous ingredients composed mainly of oxygen, ranging from 10 to 4000 ppm, excludes the amount of oxygen contained in the surface oxide film.

When the titanium implantation material is used as a fixation wire, its oxygen content should be 300 ppm or less. If the oxygen content exceeds 300 ppm, the material ductility is adversely affected and the elongation becomes less than 30%, the level of minimum necessity for a fixation wire.

Inadequate ductility will make the wire loose in the binding end on the object to be fixed, at the time of twist binding, with a wide gap left in between, as will be described later. If forcibly wound tightly around, the wire will break before the binding is complete (in the pattern of Type B as will be illustrated later). Under some circumstances the breaking occurs not in the twisted portion but at a transition point between the twisted portion and single wire portion (in the pattern of Type C). In any case, such a wire is unsuitable as a fixation wire for the living body.

Aside from insufficient binding, such a wire tends to break during the course of surgical operation, rendering it necessary to repeat the operation for a prolonged time period. In view of these and other problems, the oxygen content is desirably 200 ppm or less, more desirably 100 ppm or less. The oxygen content in this range enables the material to have sufficient ductility (elongation) to twist up to the binding end on the object to be fixed and function properly as a titanium fixation wire for the living body.

Hydrogen (H)

Under this invention the hydrogen content is specified to be 50 ppm or less. Hydrogen in a smaller amount than oxygen is as adverse in effect upon ductility. The presence of hydrogen is rather a hindrance to rapid formation of a uniform, dense oxide film. For these reasons the smaller the hydrogen content the better. If the amount of hydrogen exceeds 50 ppm, the ductility is sharply deteriorated even though the proportions of other impurities are reduced.

When such a material is used for the fixation wire purpose, as is the case with an excess of oxygen, it will wind loosely around the object to be fixed, at the time of twist binding, leaving a wide gap in between. If forcibly wound tightly around, the wire will break before the binding is complete (in the pattern of Type B as will be illustrated later). Under some circumstances the breaking occurs at a transition point between the twisted and single wire portions rather than in the twisted portion (in the pattern of Type C). In any case, the wire is unsuitable for binding use in the living body.

In addition to insufficient binding, such a wire tends to break during surgical operation, rendering it necessary to repeat the operation for an extra time period. Therefore, the hydrogen content is desirably 30 ppm or less, more desirably 20 ppm or less.

Nitrogen (N)

In this invention the nitrogen content is specified to be 200 ppm or less. Nitrogen is found about 1.5 times more adverse in effect upon ductility than oxygen. If the nitrogen content is more than 200 ppm, the ductility deteriorates sharply even though the levels of other impurities are lowered. Nitrogen rather hampers the rapid formation of a uniform, dense oxide film. For these reasons, the nitrogen content should be kept minimum.

As is the case with an excess of oxygen, a wire with an excessive nitrogen content, when used for the binding purpose, will wind loosely around the object to be fixed, at the time of twist binding to be described later, leaving a wide gap in between. If forcibly wound tightly around, the wire will break before the binding is complete (in the pattern of Type b as will be illustrated later). In some cases the breaking occurs at a transition point between the twisted and single wire portions rather than in the twisted portion (in the pattern of Type C). Thus, the wire is unsuitable for binding use in the living body.

In addition to inadequate binding, such a wire tends to break during surgical operation, making it necessary to repeat the operation for a longer time period.

In view of the foregoing, the nitrogen content is desirably 100 ppm or less, more desirably 50 ppm or less, and even more desirably 20 ppm or less. With nitrogen in this range, the wire possesses enough ductility (elongation) to wind tightly around the object to be fixed to its binding end, as the test results to be given later indicate, and it is suitable as a titanium fixation wire for the living body.

Carbon (C)

As already explained, for convenience sake, carbon was regarded as a kind of gas and was included in gaseous ingredients in this invention since carbon is removed as a gas such as CO, $CO_2$, etc. during the melting procedure such as vacuum arc melting or electron beam melting. This invention specifies the carbon content to be 400 ppm or less. Carbon occurs as an interstitial solid-solution element in titanium and serves to add strength to Ti. On the other hand, the concentration being the same, carbon reduces the ductility of the titanium material to about 0.75 time that with oxygen.

In excess of 400 ppm, carbon reduces ductility sharply despite decreases in the proportions of other impurities. Also, it rather obstructs the rapid formation of a uniform, dense oxide film. In view of these, the carbon content should be as small as possible.

When a wire with excessive carbon is used for the binding purpose, it will not wind fitly around the object to be fixed, at the time of twist binding, leaving a wide gap in between. If forcibly wound tightly around, the wire will break before the binding is complete (in the pattern of Type B as will be illustrated later). In some cases the breaking occurs at a transition point between the twisted and single wire portions rather than in the twisted portion (in the pattern of Type C). Such a wire is unsuitable for binding use in the living body.

Besides inadequate binding, such a wire also tends to break during surgical operation, making it necessary to repeat the operation for an additional time period.

The carbon content is desirably 200 ppm or less, more desirably 100 ppm or less, even more desirably 50 ppm or less. Thus, as the test results to be shown later indicate, the wire attains enough ductility (elongation) to wind around the object to be fixed, and proves suitable as a titanium fixation wire for the living body.

Ingredients Other Than the Gaseous Ingredients

In this invention, the total amount of the ingredients other than the gaseous ingredients is specified to be 100 ppm or less. For an implantation material for the living body it is important to minimize the proportions of the ingredients other than the gaseous ingredients in order to form a uniform, dense passivated film (oxide film). The inserts that are kept to be embedded inside the body, especially as bone replacements or the like for many years, must be made of a material which, when its oxide film is destroyed for one cause or another, can promptly regenerate it in vivo. The titanium implantation material according to this invention is capable of forming an oxide film quickly even at a low partial pressure of oxygen in the body.

When the material is used, in particular, as a titanium fixation wire for the living body, it is desirable for more reliable binding that the total amounts of those non-gaseous ingredients be 50 ppm or less, preferably 20 ppm or less.

Iron (Fe)

This is one of the ingredients other than said gaseous ingredients, but an exceptionally effective ingredient among the ingredients other than gaseous ones. The iron contained in titanium is, in itself, not necessarily desirable from the view point of forming a uniform, dense passivated film (oxide film). Nevertheless, it has just been found that the iron content in titanium as inserts does not have detrimental effects upon the human body for long and that iron is a favorable element which improves the tensile strength and proof stress of titanium without materially affecting the ductility. Moreover, as will be explained later, the addition of iron inhibits the growth of crystal grains and is effective in increasing the toughness by keeping the grain size small.

Fixation wires for the living body are in many cases used in small amounts for a while, and if the passivated film (oxide film) is broken in the body, its influence may often be ignored. The wires therefore are used, by preference, when mechanical strengths such as ductility, tensile strength, and proof stress have to be increased at some sacrifice of the function of forming a uniform, dense passivated film (oxide film).

Thus, when a titanium implantation material is used as a fixation wire for the living body, the amount of iron added to the material is specified to be from more than 100 to 1000 ppm. As the iron content increases, the ductility of the material decreases gradually. A wire with more than 1000 ppm iron will not wind fitly around the object to be fixed, at the time of twist binding, leaving a wide gap in between, as will be described later. If forcibly wound tightly around, the wire will break before the binding is complete (in the pattern of Type B as will be illustrated later). The breaking sometimes occurs at a transition point between the twisted and single wire portions rather than in the twisted portions (in the pattern of Type C). Such a wire is unsuitable for binding use in the living body. Hence the upper limit of Fe addition is 1000 ppm.

The iron content is desirably from more than 100 to 800 ppm, more desirably from more than 100 to 600 ppm. Thus, as the test results to be shown later indicate, the wire attains enough ductility (elongation) to wind around the object to be fixed, and proves suitable as a titanium fixation wire for the living body.

Tensile Strength and Proof Stress

Titanium implantation materials for the living body have thus far been described mostly with regard to the ingredients to be contained therein. As bone replacements and reinforcements, and also as fixation wires for fixation and binding used in the living body, the materials are required to have sufficient tensile strength and proof stress.

The tensile strength and proof stress to be possessed desirably are at least 175 MPa and 70 MPa, respectively.

As noted above, oxygen usually adds to the strength of titanium, and its presence in some amount is rather beneficial. Excess oxygen, however, tends to deprive titanium of its high ductility, workability, and flexibility that are requisites for an implantation material for the living body. Especially with a fixation wire, sacrificing its ductility for strength should be avoided because of the danger of wire breaking.

As will be appreciated from the foregoing, strength and high ductility are indispensable for implantation materials for the living body. In general, a material with tensile strength and proof stress of at least 175 MPa and 70 MPa, respectively, is practically not objectionable but is suitable as an implantation material for the body.

Where an implantation material is to have a maximum strength, as in use at a bone joint subject to a heavy load, the end is achieved by redesigning the structure, increasing the diameter of the piece to be implanted, or enhancing its strength by plastic working. Any of these approaches may be adopted as needed. The implantation materials according to this invention fully satisfy these conditions.

Average Crystal Grain Diameter

In this invention, the average crystal grain diameter (called hereinafter as grain size) desirably ranges from 2 to 150 $\mu$m. The toughness of the material increases in inverse proportion to the grain size. In reality, however, a material with a grain size of less than 2$\mu$m is difficult to produce. If produced, the material would retain some partial distortion and have reduced ductility. Conversely when the average grain size is large, especially above 150 $\mu$m, the number of crystal grains decreases to such an extent that localized deterioration of ductility results. This is undesirable either.

Production Process

The details of production process will now be described.

A titanium material after the compositional adjustment of the ingredients as specified above is melted and cast to a titanium ingot. In order to reduce the oxygen, nitrogen, hydrogen, carbon, and other impurities as gaseous ingredients to predetermined amounts or less, techniques such as vacuum are melting and electron beam melting may be used. The titanium ingot thus obtained is forged, according to the necessity, and then rolled or pressed. If necessary, it is swaged or drawn and then machined to a desired shape. When the material is worked into a wire, it is drawn to a given wire size, e.g., 1.7, 1.0, 0.8, or 0.4 mm in diameter. To obtain a wire of a desired diameter, wire drawing is carried out with a suitable die chosen for the size. The cross sectional area reduction is about 30 to 90%.

During the course of working, process annealing is carried out (in a temperature range of 400° to 900° C. preferably 500° to 700° C., more preferably 550° to 650° C., for about 10 seconds to 5 hours).

As an alternative to the above process, it is possible to roll the stock into a thin plate, slit it into square rods, round off the corners with a grinder or the like, and then swage and draw each work into a wire .

After final working, the work is finally annealed in a temperature range of 400° to 900° C., preferably 500° to 700° C. more preferably 550° to 650° C., for about 10 seconds to 5 hours. Through this working and annealing, the work is adjusted to a desire grain size (e.g., an average grain size of 2 to 150 $\mu$m). The process annealing and final annealing may be performed in either continuous or batch operation. An implantation material of a desired shape is thus produced.

To form an oxide film on the surface, the material is subjected to anodizing, thermal oxidation, molten salt oxidation, or other means following the conclusion of plastic working or annealing. In this manner a uniform and dense oxide film is formed.

The process described above provides an excellent implantation material for the living body which possesses sufficient strength and ductility as a bone replacement or reinforcement or as a fixation wire to be implanted, exhibits outstanding corrosion resistance in the body, and which, if its oxide film is destroyed, can readily regenerate the film in the body.

EXAMPLE 1 AND COMPARATIVE EXAMPLE 1

Specimens of this invention suitable as implantation materials for the living body (Example) and specimens of CP-Ti (titanium) and stainless steel (SUS316L) both of which contained beyond the upper limits of the ingredients other than the gaseous ingredients such as iron (Comparative Example) are compared below.

Those titanium specimens were prepared in the following way. Titanium materials after the compositional adjustments were melted by electron beam melting and cast into ingots of respective compositions. Those ingots were forged and. cold rolled into plates. During the working, they were subjected to process annealing at proper points in a temperature range of 400° to 900° C. Further, after final cold working, they were finally annealed in a temperature range of 400° to 900° C. to obtain recrystallization textures. The stainless steel (SUS316L) used in Comparative Example was a commercially available one.

The plates so obtained were cut into blocks each measuring 10×10×5 mm. Wires of the same materials were spot welded, one for each, to the blocks, and the wired blocks were embedded in pieces of a water-insoluble polymer. The pieces were abraded using a wet abrasive paper to expose the block side of 10×10 mm. That side of each block was used as a surface for measurements.

Analytical values of the chemical compositions of those specimens are given in Table 1.

In Table 1, Specimen 1 (UP-Ti: Ultra Purity Ti) and Specimen 2 (HP-Ti: High Purity Ti) show the chemical analysis values of Example of this invention and Specimen 3 (CP-Ti: Commercial Purity Ti) and Specimen 4 (stainless steel) show the chemical analytical values of Comparative Example. Specimen 3 was high in iron (Fe) content, containing 0.03 wt % (300 ppm) Fe.

Corrosion Resistance Tests (Anodic Polarization Curves)

The measuring surface of each titanium specimen was polished with a wet abrasive paper to #600, chemically polished with a hydrofluoric acid-hydrogen peroxide-water polishing solution, washed with pure water, and immersed in a measuring solution with care taken not to expose it to the air. The stainless steel (SUS316L) specimen was buffed on the measuring side to a mirror surface and then, like the titanium specimens, washed with pure water and immersed in a measuring solution without direct contact with the air.

The measuring conditions were as follows.

Electrolyte: Hank's solution deoxygenated with Ar

Bath temperature: 310 K.

Reference electrode: Ag/AgCl

Counter electrode: Pt

Potential sweep rate: 40 mV/min

The results are shown in FIG. 1.

Results of Corrosion Resistance Tests

The anodic polarization curves represent the titanium and stainless steel (SUS316L) specimens in the state where there was no passivated film on their initial surfaces. As FIG. 1 clearly indicates, Specimens 1 (UP-Ti) and Specimen 2 (HP-Ti) of titanium in Example of this invention were on the nobler side in rest potential than Specimen 3 (CP-Ti) of titanium in Comparative Example. Moreover, Specimens 1 (UP-Ti) and Specimen 2 (HP-Ti) show lower current values than Specimen 3 with the formation of a corrosion resistant film. These demonstrate the higher corrosion resistance of Specimens 1 and 2 according to this invention.

Immediate rise of the current value of the stainless steel (SUS316L) of Specimen 4 is a proof that the stainless steel (SUS316L) is inferior in corrosion resistance to any of the titanium materials.

Further, as is obvious from FIG. 1, titanium Specimens 1 and 2 of this invention show sharp rises of current at the early stage of polarization, indicating rapid formation of an oxide film. This means that the specimens are ideal implantation materials for the living body because of their outstanding feature of reforming the oxide film, even if it is broken in the body, faster than the other corrosion resistance materials do.

EXAMPLE 2 AND COMPARATIVE EXAMPLE 2

Specimens of the same titanium materials and stainless steel (SUS316L) as those of Example 1 and Comparative Example 1 were prepared and their measuring surfaces were finished following the same procedure. They were further

TABLE 1

Chemistry of UP-Ti, HP-Ti, CP-Ti and SUS316L (wt. %)

|  |  | Ti | O | N | Fe | Ni | Cr | Mo | Sn | Al |
|---|---|---|---|---|---|---|---|---|---|---|
| Specimen 1 | UP-Ti | bal. | 0.015 | <0.001 | <0.00001 | <0.00001 | <0.00001 | <0.000001 | <0.00001 | ≦0.00005 |
| Specimen 2 | HP-Ti | bal. | 0.016 | <0.001 | 0.0002 | 0.0001 | <0.0001 | <0.000001 | 0.0001 | ≦0.0001 |
| Specimen 3 | CP-Ti | bal. | 0.070 | <0.010 | 0.03 | 0.00011 | 0.00009 | <0.001 | <0.00001 | 0.00018 |
| Specimen 4 | SUS316L | <0.01 | 0.004 | 0.046 | bal. | 12.54 | 18.00 | 2.55 | 0.003 | 0.008 |

|  | Cu | Mn | Zr | Co | Na | K | U | Th |
|---|---|---|---|---|---|---|---|---|
| Specimen 1 | ≦0.00002 | <0.00001 | <0.001 | <0.00001 | ≦0.000002 | ≦0.000002 | ≦0.00000001 | ≦0.00000001 |
| Specimen 2 | 0.000036 | <0.0001 | <0.001 | <0.00001 | ≦0.000002 | ≦0.000002 | ≦0.00000001 | ≦0.00000001 |
| Specimen 3 | 0.00013 | <0.00001 | <0.001 | <0.00003 | <0.000001 | <0.000001 | 0.00021 | 0.00003 |
| Specimen 4 | 0.006 | 1.24 | <0.005 | 0.02 | 0.00004 | <0.00005 | 0.00000024 | 0.00000065 | surface treated in the following way to obtain specimens for the present Examples. They were identical in chemical compositions with the specimens of Example 1 and Comparative Example 1. The only difference is that in this case the oxide film was formed by anodizing in advance.

The titanium specimens were anodized in an oxalic acid-sulfuric acid bath using stainless steel SUS304 as a cathode. The oxidation voltage at that time was 6.5 V. After the anodizing, the specimens were washed with pure water and placed in a measuring solution lest it come in direct contact with the air. The stainless steel (SUS316L) specimen was immersed in nitric acid for 30 minutes, washed with pure water, and immersed in a measuring solution without direct contact with the air, in conformity with the procedure of ASTM F-86.

The measuring conditions were as follows.

Electrolyte: Hank's solution deoxygenated with Ar

Bath temperature: 310 K.

Reference electrode: Ag/AgCl

Counter electrode: Pt

Potential sweep rate: 40 mV/min

Figure 2:
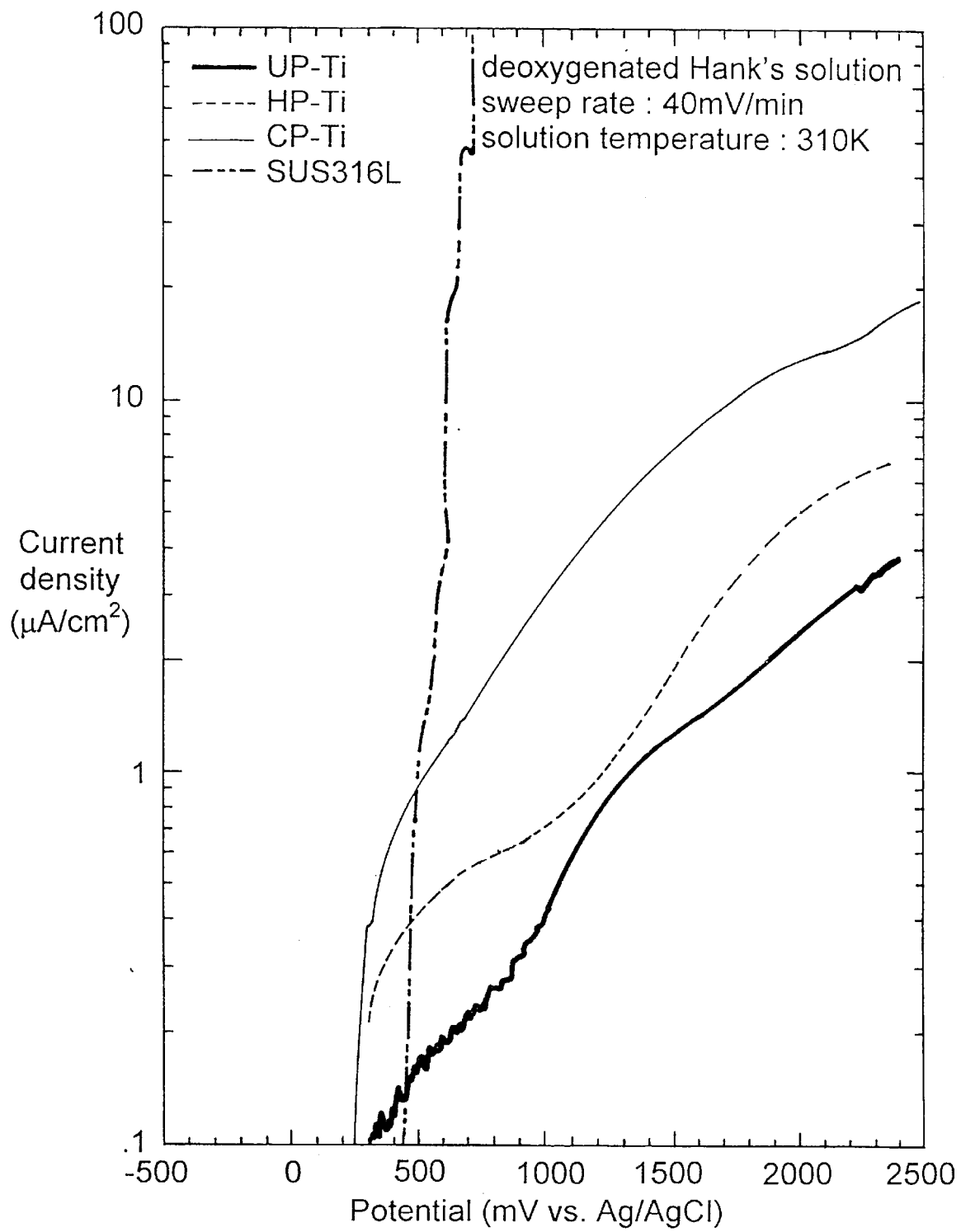
FIG. 2 is a graph showing anodic polarization curves of titanium and stainless steel specimens of Example 2 and Comparative Example 2 which had a passivated film each formed on the surface by anodizing.

The results are shown in FIG. 2.

Results of Corrosion Resistance Tests

The anodic polarization curves represent the titanium and stainless steel (SUS316L) specimens in the state where there was a passivated film formed on their surfaces. As FIG. 2 shows, Specimens 1 and 2 of titanium in Example of this invention were on the nobler side in rest potential than titanium Specimen 3 of Comparative Example. Moreover, they show lower current values than Specimen 3 in forming a corrosion-resistant film. These attest the higher corrosion resistance of Specimens 1 and 2 according to this invention.

Although the stainless steel (SUS316L) of Specimen 4 in Comparative Example was on the nobler side than the titanium materials, the immediate rise of the current value is a proof that the stainless steel is inferior in corrosion resistance to any of the titanium materials. Further, as can be seen from FIG. 2, titanium Specimens 1 and 2 of this invention caused moderate rises of current compared with the titanium specimen of Comparative Example, indicating their superiority in corrosion resistance.

As is manifest from the above, the titanium materials of this invention are far superior in corrosion resistance to the other titanium and stainless steel (SUS316L) materials and is quicker to form an oxide film. This means that they are ideal implantation materials for the living body because of their outstanding feature of reforming the oxide film, if it is broken in the body, faster than the other corrosion resistance materials do.

EXAMPLE 3 AND COMPARATIVE EXAMPLE 3

An Example of this invention as applied to titanium fixation wires for the living body will be compared below with a Comparative Example.

Compositionally adjusted titanium materials were melted and cast into titanium ingots. Electron beam melting was used in removing gaseous ingredients, such as oxygen, nitrogen, hydrogen, and carbon, as impurities from the ingots.

The titanium ingots so obtained were subjected to forging, channel rolling, swaging, and wire drawing to form wires 1.0 and 0.8 mm in diameter. The rates of area reduction were about 30 to 90%. During the working, the works were process annealed in the temperature range of 400° to 900° C. and, after final working, finally annealed in the temperature range of 400° to 900° C. The average grain sizes were 2 to 150$\mu$m.

The compositional analytical values of the titanium wire specimens thus obtained are listed in Table 2. The values for Specimens 1–19 in Table 2 are means of the values of 20 samples each. The compositional analytical values are given provided that the units digit of 5 and over was counted as ten and the units digit of 1 to 4 was cut away as zero.

As an alternative to the above process, each stock was rolled into a sheet, slit into square rods, with the corners rounded off with a grinder, and then, in the same manner as above, swaged and drawn into a wire. The wires so made showed practically no distinction in performance from the above specimens provided their compositional analytical values fell within the ranges specified by this invention.

As regards the annealing temperature ranges of 500° to 700° C. and 550° to 650° C. and also in the variations of the average grain size, the specimens whose values deviated from the "more desirable" or "preferable" numerical ranges tended to show somewhat more dispersions in properties than the specimens whose values were in those ranges. Those deviating specimens, however, displayed little differences in properties as long as their compositional analytical values came within the ranges of this invention.

For comparison purposes, titanium wires were made by the same manufacturing process and with the same compositional adjustments of the impurities.

The compositional analytical values of the comparative specimens are also listed in Table 2. The numerical values of Specimens 20 to 30 given in the table likewise are means of 20 samples. The numerical values of analysis again are given. Also herein, the units digit of 5 and over was counted as ten and the units digit of 1 to 4 was cut away as zero.

TABLE 2

Changes in elongation and gap* with changes in impurities contents

| | | | | | | | Non-gas | Elong. | Gap (mm) | |
| --- | --- | --- | --- | --- | --- | --- | --- | --- | --- | --- |
| | | Ti | O | C | N | H | Impurities | (%) | 0.8 | 1.0 |
| Specimen in | 1 | bal. | 140 | 10 | 10 | <10 | <10 | 51.8 | 0.0 | 0.0 |
| Example of | 2 | bal. | 170 | 20 | 10 | <10 | <10 | 51.0 | 0.0 | 0.0 |
| the | 3 | bal. | 200 | 10 | 10 | <10 | <10 | 41.8 | 0.2 | 0.2 |
| invention | 4 | bal. | 250 | 10 | 10 | <10 | <10 | 43.6 | 0.3 | 0.2 |
| | 5 | bal. | 150 | 30 | 10 | <10 | <10 | 44.8 | 0.2 | 0.3 |
| | 6 | bal. | 140 | 70 | 10 | <10 | <10 | 45.6 | 0.4 | 0.4 |
| | 7 | bal. | 140 | 160 | 10 | <10 | <10 | 34.1 | 0.5 | 0.7 |
| | 8 | bal. | 140 | 10 | 20 | <10 | <10 | 49.2 | 0.0 | 0.0 |
| | 9 | bal. | 140 | 10 | 50 | <10 | <10 | 36.7 | 0.7 | 0.6 |

TABLE 2-continued

Changes in elongation and gap* with changes in impurities contents

|  |  | Ti | O | C | N | H | Non-gas Impurities | Elong. (%) | Gap (mm) 0.8 | 1.0 |
|---|---|---|---|---|---|---|---|---|---|---|
|  | 10 | bal. | 150 | 20 | 130 | <10 | <10 | 41.1 | 0.6 | 0.4 |
|  | 11 | bal. | 140 | 10 | 10 | 20 | <10 | 44.2 | 0.2 | 0.2 |
|  | 12 | bal. | 140 | 10 | 10 | 30 | <10 | 43.1 | 0.4 | 0.4 |
|  | 13 | bal. | 140 | 20 | 10 | 40 | <10 | 32.6 | 0.5 | 0.7 |
|  | 14 | bal. | 140 | 10 | 10 | <10 | 20 | 51.7 | 0.0 | 0.0 |
|  | 15 | bal. | 150 | 10 | 10 | <10 | 60 | 34.6 | 0.4 | 0.8 |
|  | 16 | bal. | 150 | 10 | 10 | <10 | 80 | 34.2 | 0.8 | 0.7 |
|  | 17 | bal. | 170 | 20 | 20 | <10 | 20 | 41.3 | 0.0 | 0.1 |
|  | 18 | bal. | 210 | 50 | 50 | 20 | 40 | 34.2 | 0.4 | 0.8 |
|  | 19 | bal. | 240 | 130 | 130 | 20 | 80 | 31.8 | 0.8 | 0.7 |
| Specimen in | 20 | bal. | 680 | 10 | 10 | <10 | <10 | 16.8 | 4.8 | 5.6 |
| Comparative | 21 | bal. | 470 | 20 | 10 | <10 | <10 | 22.2 | 2.1 | 2.8 |
| Example | 22 | bal. | 400 | 10 | 10 | <10 | <10 | 17.4 | 2.2 | 3.2 |
|  | 23 | bal. | 140 | 430 | 10 | <10 | <10 | 24.3 | 1.3 | 1.6 |
|  | 24 | bal. | 140 | 480 | 10 | <10 | <10 | 25.1 | 2.8 | 2.5 |
|  | 25 | bal. | 150 | 10 | 250 | <10 | <10 | 23.9 | 4.6 | 5.1 |
|  | 26 | bal. | 140 | 10 | 320 | <10 | <10 | 24.5 | 6.0 | 7.6 |
|  | 27 | bal. | 140 | 10 | 10 | 60 | <10 | 22.1 | 2.2 | 1.8 |
|  | 28 | bal. | 140 | 20 | 10 | 70 | <10 | 18.3 | 2.4 | 2.6 |
|  | 29 | bal. | 150 | 10 | 10 | <10 | 130 | 27.6 | 1.6 | 2.0 |
|  | 30 | bal. | 140 | 10 | 10 | <10 | 250 | 25.2 | 3.5 | 3.4 |

Figure 13A:
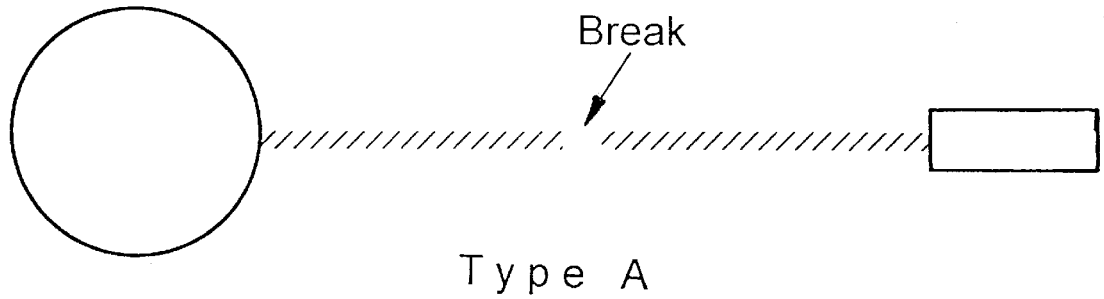
FIGS. 13(a), 13(b) and 13(c) are explanatory views of breaks classified into types A, B and C.
Figure 13B:
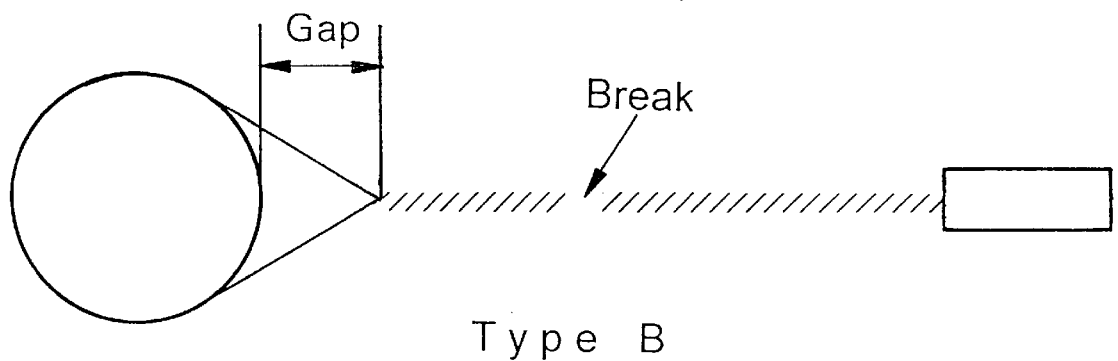
Figure 13:
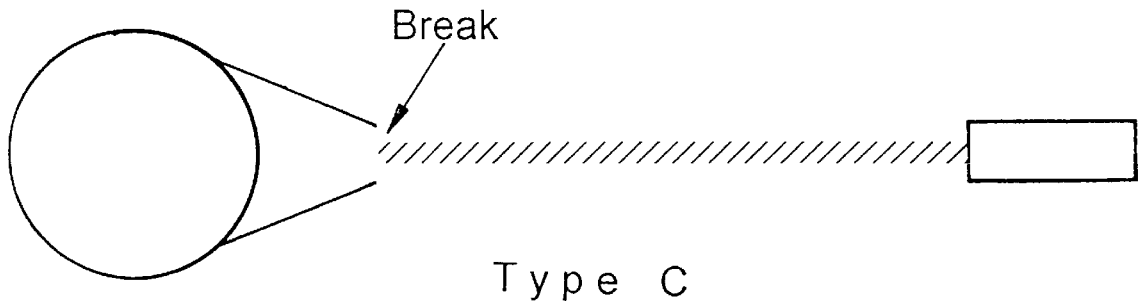

*Refer to FIG. 13,
Speed: 60 rpm

With these specimens, the following tests were conducted.
(1) Tensile Test (Measurement of Elongation)
Two kinds of wires with different gage diameters were tested for tensile strength.
  Length between gage marks: 70 mm
  Tensile testing speed: 10 mm/min
  Gage diameters: 1.0 and 0.8 mm
(2) Twist Test
Each set of two wires with different diameters were subjected to a twist test.
  Jig as object of winding: round bar-fixing jig 20 mm in diameter
  Rotational speed: 60 rpm
  No. of twists: 30 or more
  Wire diameters: 1.0 and 0.8 mm The results of the tensile tests (measurements of elongation) thus performed are summarized in Table 2 and FIGS. 3 to 7.

As will be understood from Table 2, Specimens 1 to 19 in Example of this invention, without exception, showed good ductility with elongation values of more than 30%. The ductility was high especially when the amounts of the gaseous ingredients they contained were: 200 ppm or less oxygen, 30 ppm or less hydrogen, 100 ppm or less nitrogen, 100 ppm or less carbon, and 50 ppm or less impurities other than the gaseous ingredients such as iron. More preferable ranges are 100 ppm or less oxygen, 20 ppm or less hydrogen, 20 ppm or less nitrogen, 50 ppm or less carbon, and 20 ppm or less impurities other than the gaseous ingredients such as iron. With the latter ranges, extremely high ductility is ensured.

In contrast to the above, it will be seen that all of Specimens 20 to 30 presented as Comparative Example were quite inferior in ductility, with elongation values of less than 30%. None of Specimens 20 to 30 are suitable as titanium fixation wires for the living body, since the compositions of the comparative specimens exceeds one or more of 300 ppm oxygen, 50 ppm hydrogen, 200 ppm nitrogen, 400 ppm carbon, and 100 ppm impurities other than the gaseous ingredients such as iron.

Figure 3:
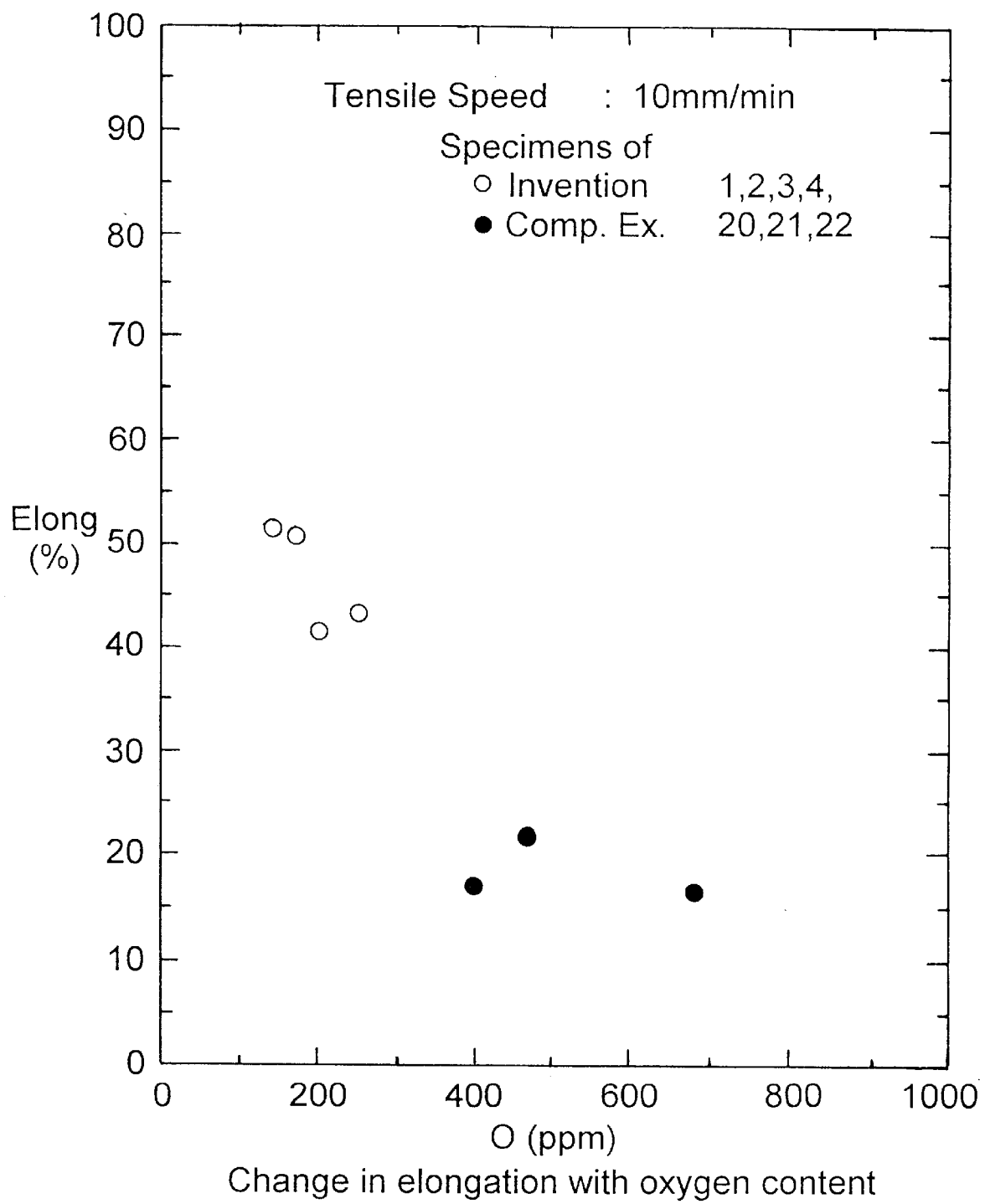
FIG. 3 is a graph showing changes in elongation with the oxygen contents in Example 3 and Comparative Example 3.

FIG. 3 shows changes in elongation with the oxygen contents of Specimens 1 to 4 in Example of the invention and of Specimens 20 to 22 of Comparative Example.

Figure 4:
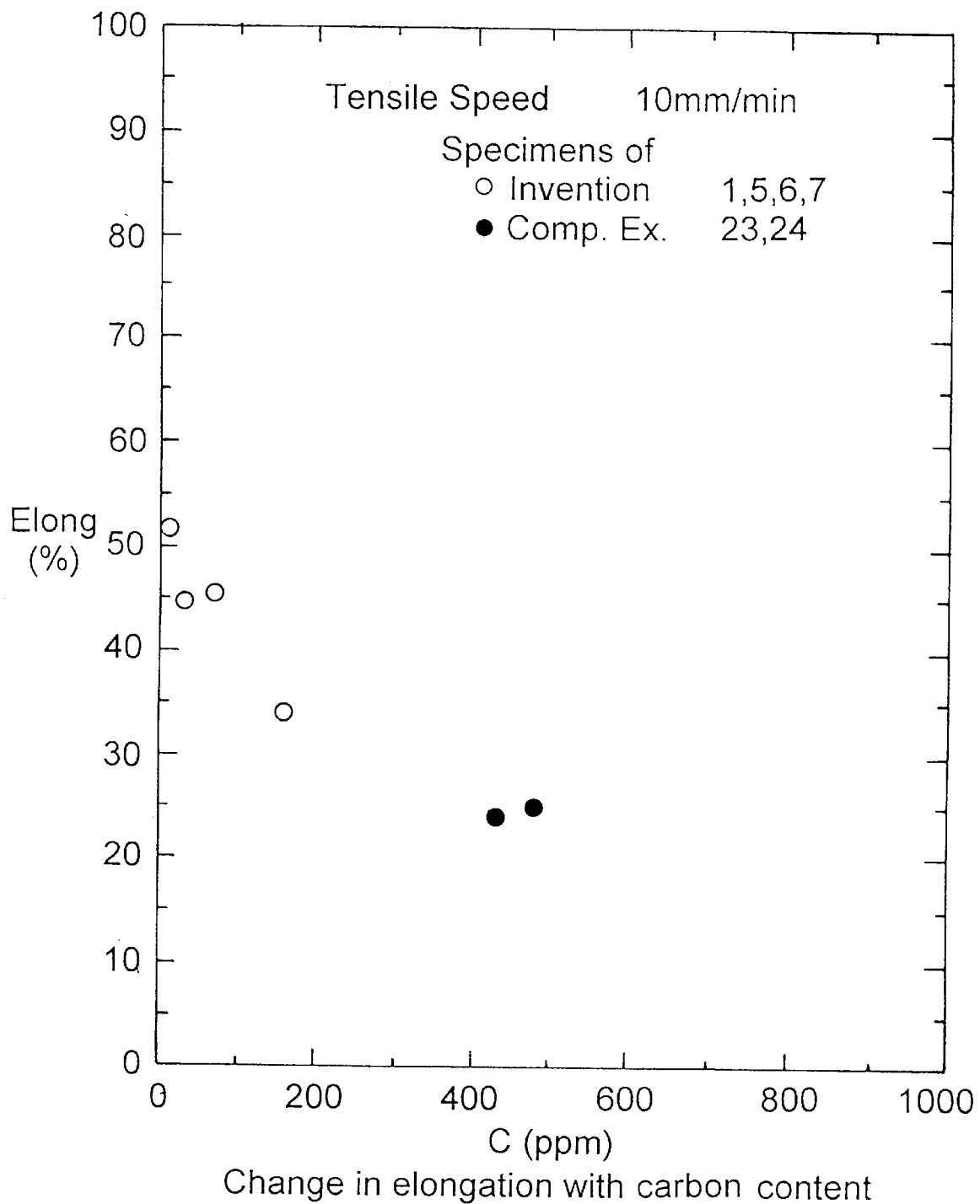
FIG. 4 is a graph showing changes in elongation with the carbon contents in Example 3 and Comparative Example 3.

FIG. 4 shows changes in elongation with the carbon contents of Specimens 1, 5, 6, and 7 and of Specimens 23 and 24 of Comparative Example.

Figure 5:
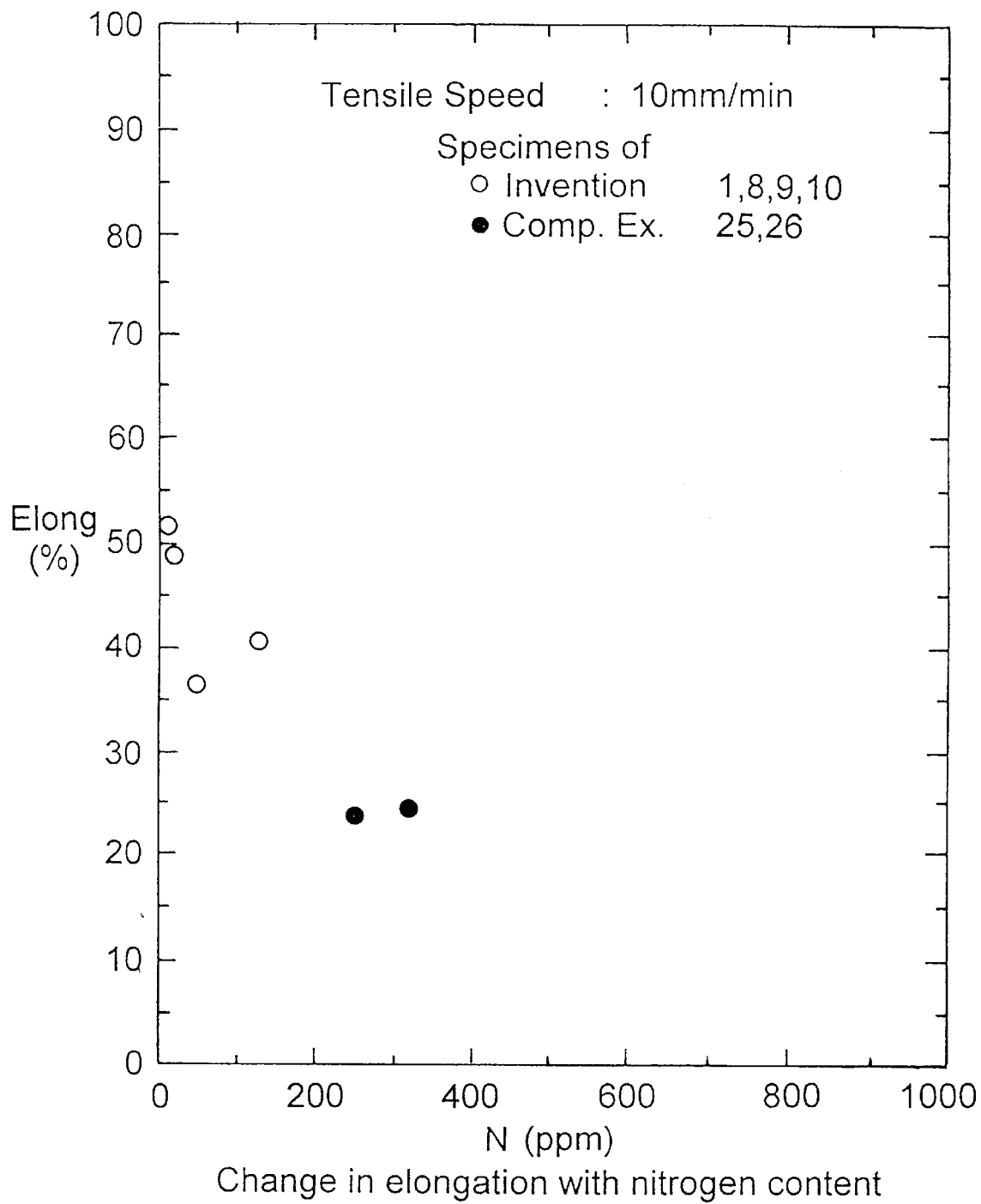
FIG. 5 is a graph showing changes in elongation with the nitrogen contents in Example 3 and Comparative Example 3.

FIG. 5 shows changes in elongation with the nitrogen contents of Specimens 1, 8, 9, and 10 and of Specimens 25 and 26 of Comparative Example.

Figure 6:
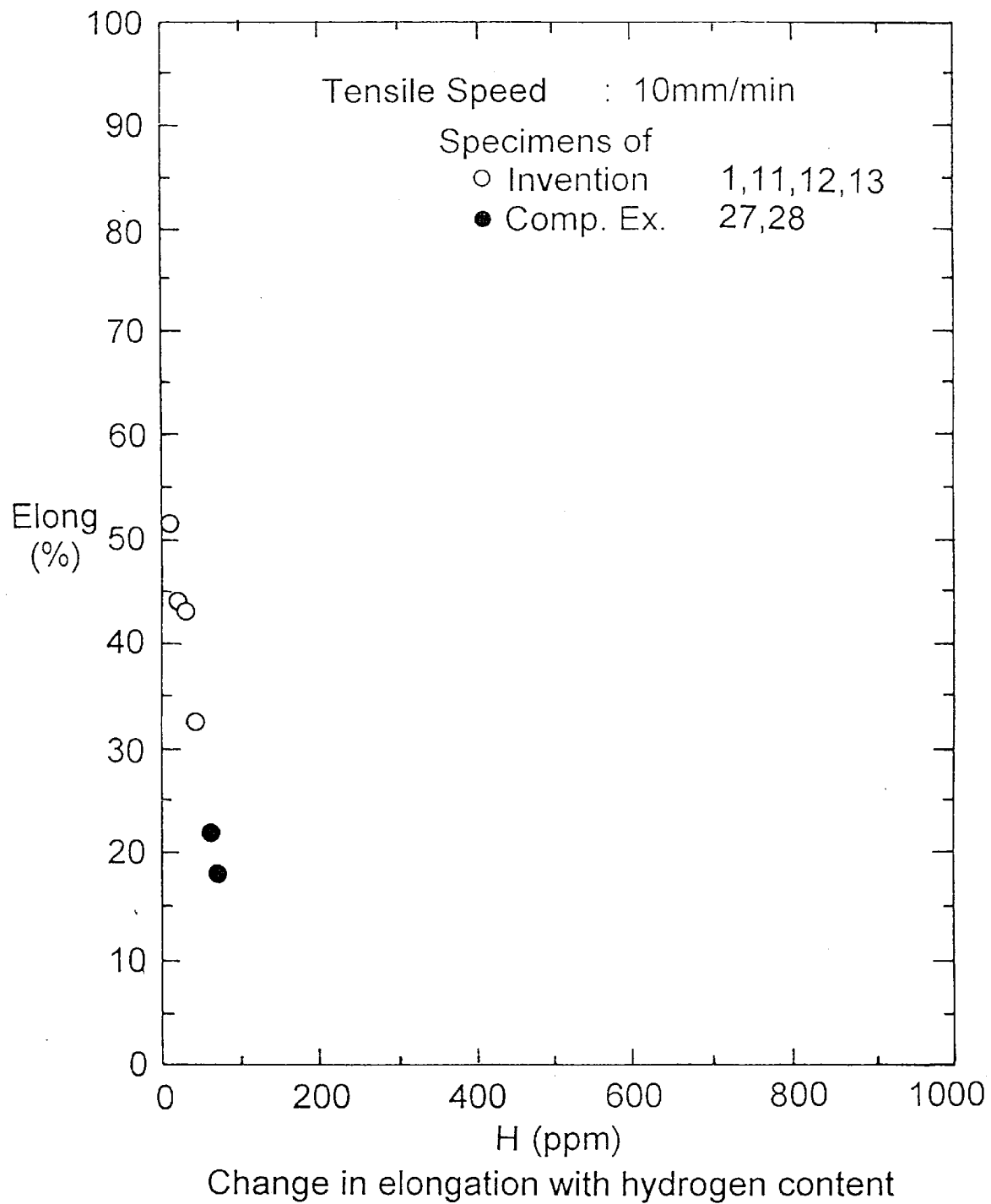
FIG. 6 is a graph showing changes in elongation with the hydrogen contents in Example 3 and Comparative Example 3.

FIG. 6 shows changes in elongation with the hydrogen contents of Specimens 1, 11, 12, and 13 and of Specimens 27 and 28 of Comparative Example.

Figure 7:
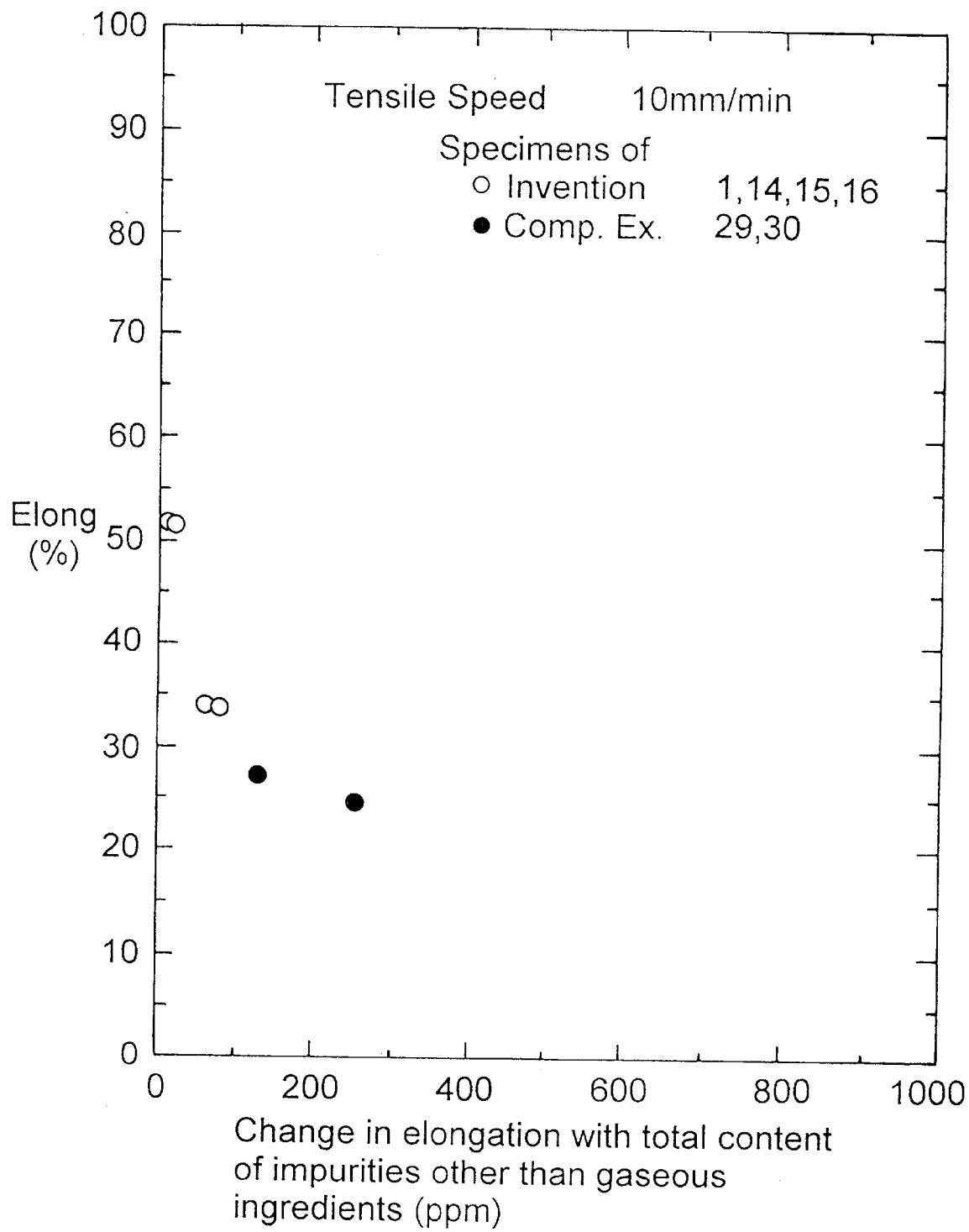
FIG. 7 is a graph showing changes in elongation with the contents of impurities other than the gaseous ingredients in Example 3 and Comparative Example 3.
Figure 8:
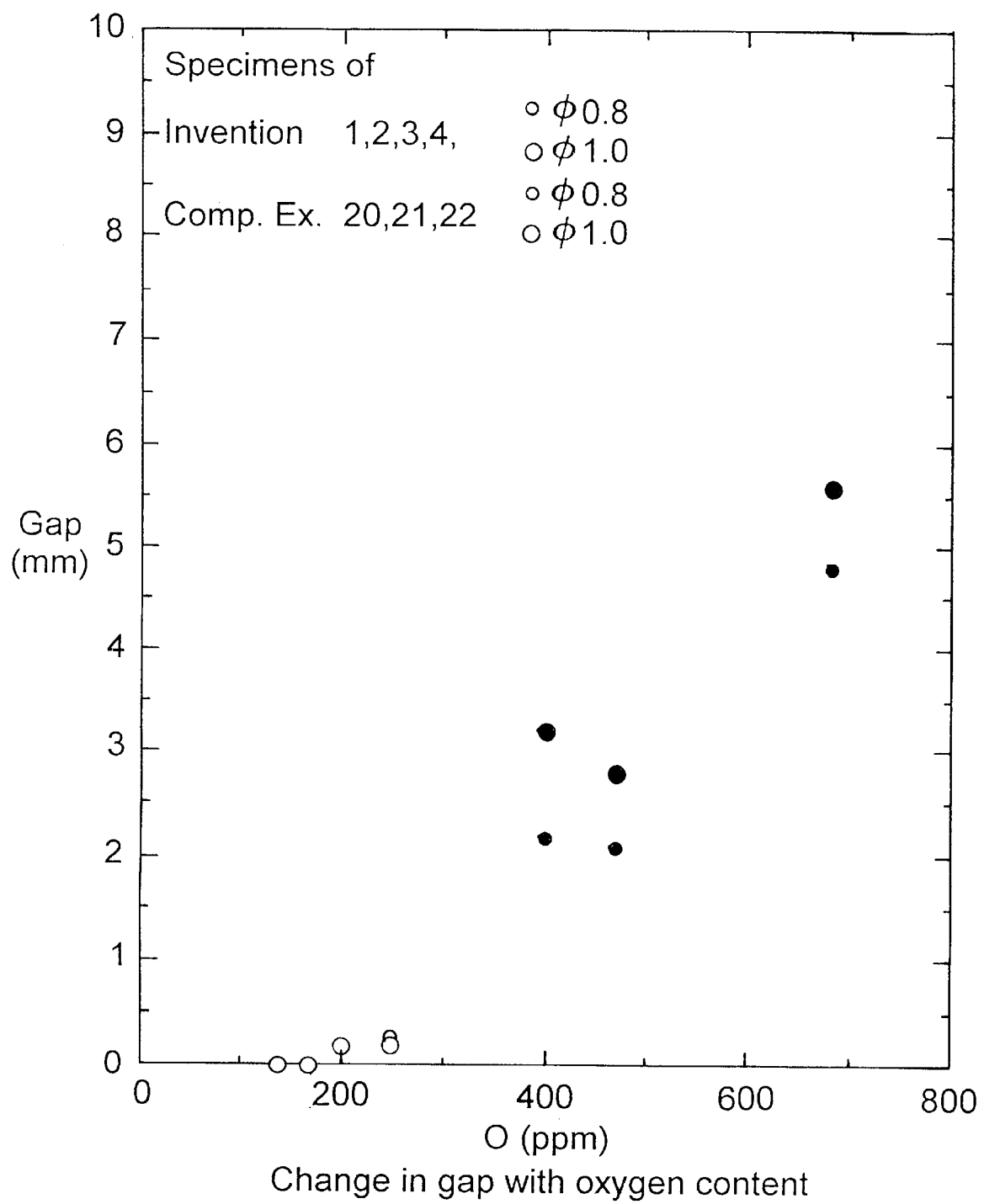
FIG. 8 is a graph showing changes in gap with the oxygen contents in Example 3 and Comparative Example 3.
Figure 9:
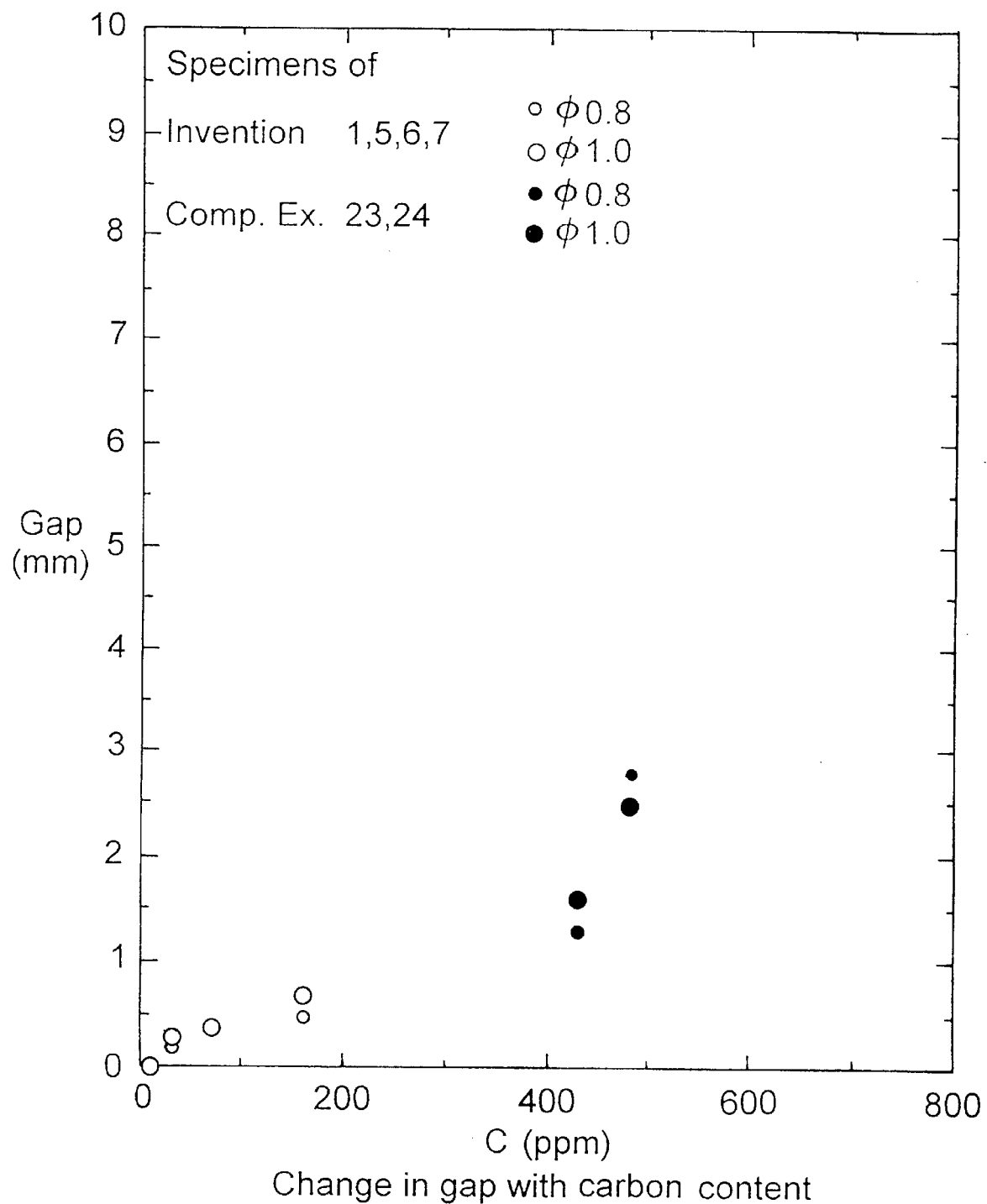
FIG. 9 is a graph showing changes in gap with the carbon contents in Example 3 and Comparative Example 3.
Figure 10:
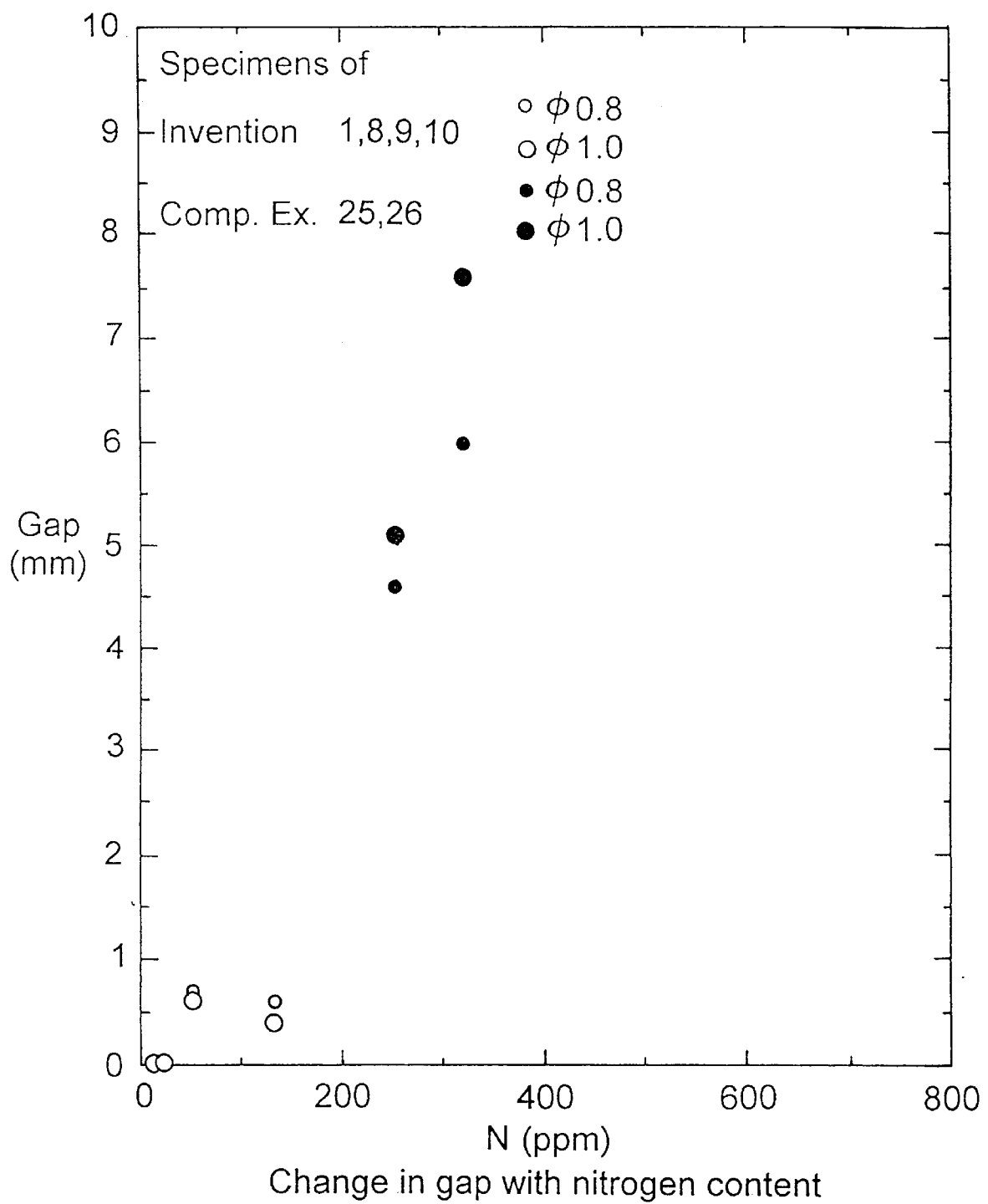
FIG. 10 is a graph showing changes in gap with the nitrogen contents in Example 3 and Comparative Example 3.
Figure 11:
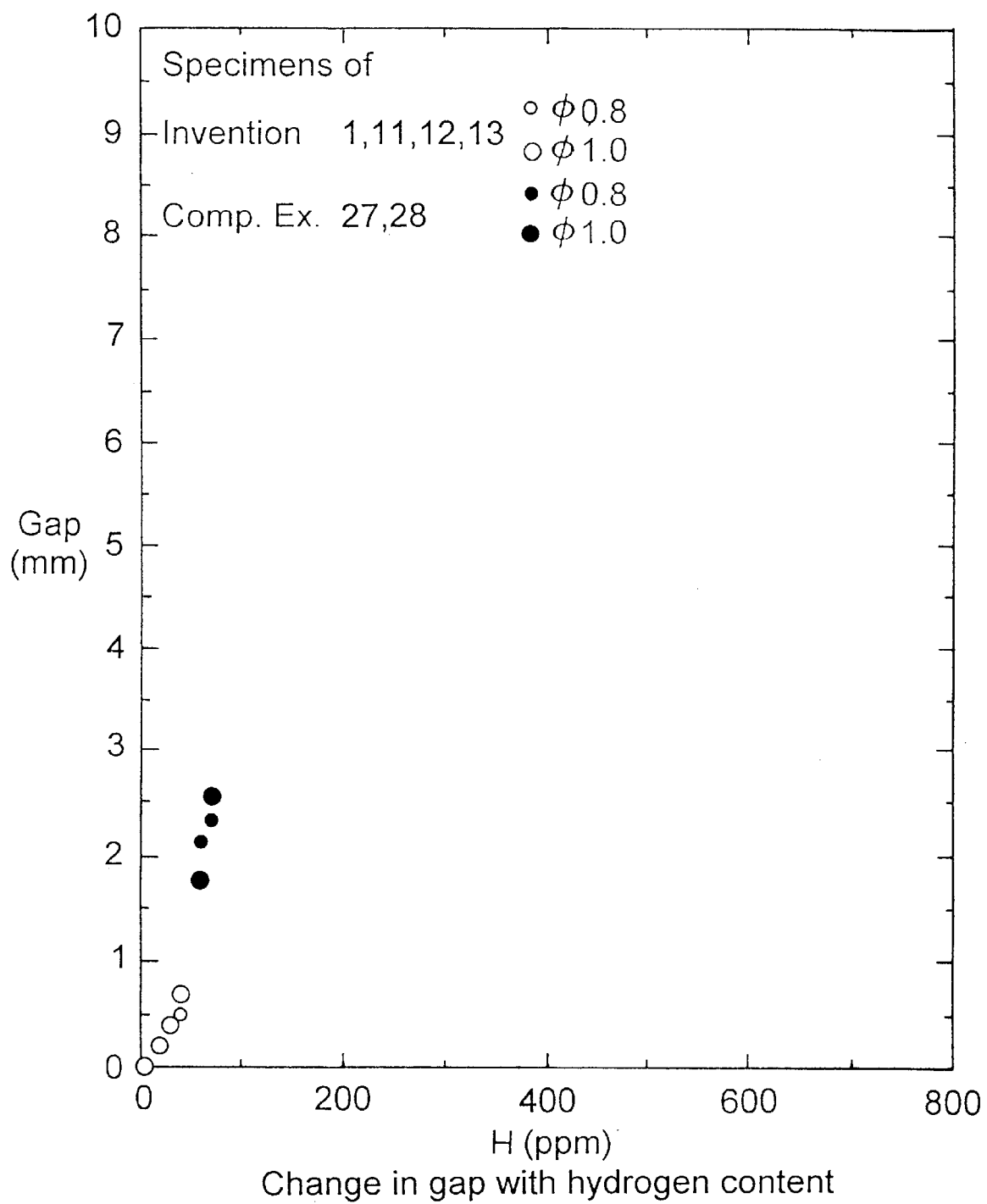
FIG. 11 is a graph showing changes in gap with the hydrogen contents in Example 3 and Comparative Example 3.
Figure 12:
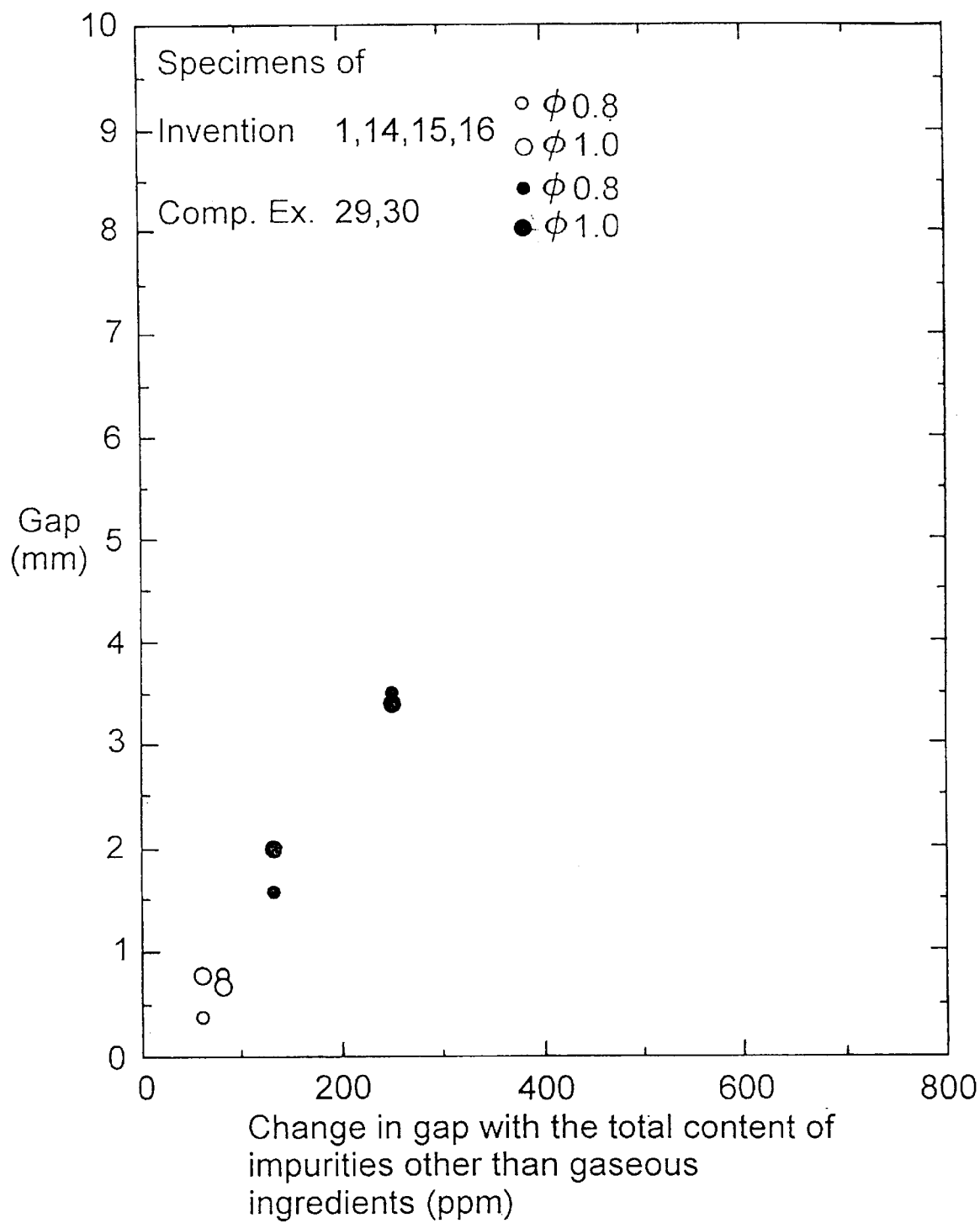
FIG. 12 is a graph showing changes in gap with the contents of impurities other than the gaseous ingredients in Example 3 and Comparative Example 3.

FIG. 7 shows changes in elongation with the amounts of impurities other than the gaseous ingredients contained in Specimens 1, 14, 15, and 16 and in Specimens 29 and 30 of Comparative Example. It is quite clear that the specimens of the invention exhibit better elongations than the comparative specimens.

As for the tensile strength and proof stress as measured in tensile tests, they gave values of more than 175 MPa and 70 MPa, respectively, and, without practical drawbacks, they were suitable as fixation wires for the living body.

The results of torsion tests are shown in Tables 2 and 3 and FIGS. 8 through 12, and the patterns of breaks are illustrated in FIG. 13.

TABLE 3

Patterns* of break in torsion tests

|  |  | φ 1.0 | φ 0.8 |
|---|---|---|---|
| Specimen in | 1 | A | A |
| Example of | 2 | A | A |
| the | 3 | A | A |
| invention | 4 | A | A |

TABLE 3-continued

Patterns* of break in torsion tests

| | | φ 1.0 | φ 0.8 |
|---|---|---|---|
| | 5 | A | A |
| | 6 | A | A |
| | 7 | A | A |
| | 8 | A | A |
| | 9 | A | A |
| | 10 | A | A |
| | 11 | A | A |
| | 12 | A | A |
| | 13 | A | A |
| | 14 | A | A |
| | 15 | A | A |
| | 16 | A | A |
| | 17 | A | A |
| | 18 | A | A |
| | 19 | A | A |
| Specimen of | 20 | C | B |
| Comparative | 21 | B | B |
| Example | 22 | B | B |
| | 23 | B | B |
| | 24 | B | C |
| | 25 | B | B |
| | 26 | B | B |
| | 27 | B | B |
| | 28 | B | C |
| | 29 | B | B |
| | 30 | C | B |

Speed: 60 rpm
*Classified by Types A, B, and C as follows: (Refer to FIG. 13.)
Gap
A < 1.0
B ≧ 1.0
C = broken at a transition point between a twist and a straight line portion.

FIG. 13 shows wires in twist tests wound around bar-fixing jigs 20 mm in diameter each at a speed of 60 rpm.

Type A represents a break pattern of a wire tightly wound around the jig and twisted up to the binding end on the object with little gap (less than 1.0 mm). When the wire breaks (due to overtwisting), the break occurs midway the twisted portion, where the working strains are concentrated. This represents a favorable pattern of break.

In Type B the wire breaks while it is unable to be wound completely and twisted up to the binding end on the jig (with a gap of more than 1.0 mm). This results from inadequate ductility of the wire. In this case, slackening can take place in the binding.

In Type C a break occurs at a transition point between the twisted portion and the single wire portion. The fixation wire in this state is utterly inadequate.

As is obvious from Table 3, Specimens 1 to 19 embodying this invention, with both diameters of 1.0 and 0.8 mm, showed break patterns of Type A, indicating that they were fitly wound round the jigs, twisted up to the binding end on the objects with little gaps (less than 1.0 mm) in between.

The particulars of gaps formed by wires in winding around jigs are shown in Table 2 and FIGS. 8 through 12. Specimens 1 to 19 left gaps of less than 1.0 mm, indicating that the higher the ductility the better. Some specimens could be twisted up to the wire-binding end on the jigs closely enough to leave no gap in between.

Specimens 20 to 30 of comparative Example, by contrast, broke in the patterns of either Type B or C. As Table 2 and FIGS. 8 to 12 illustrate, the wires broke before they were twisted up to the binding ends on jigs (leaving a gap of more than 1.0 mm) or broke at a transition point between the twisted and single wire portions. These wires are unsuitable as titanium fixation wires for the living body. They have the danger of being broken during or after the surgical operation or producing inadequate binding.

The titanium fixation wires for the living body according to this invention described in Example 3 are intended for binding of bones and artificial bones in the human body. They have sufficient ductility (elongation) to be wound around an object to be fixed and twisted up to the binding end of the object. They permit easy and firm binding during the course of surgical operation and exhibit an eminent feature of great safety in the body. They also display their particularly advantageous performance in fixing grafted bones and the like.

EXAMPLE 4 AND COMPARATIVE EXAMPLE 4

This invention is further illustrated by another Example (as compared with a Comparative Example) as follows.

Compositionally adjusted titanium materials were melted and cast into titanium ingots. Electron beam melting was used to remove gaseous ingredients, such as oxygen, nitrogen, hydrogen, and carbon, as impurities from the ingots.

The titanium ingots so obtained were subjected to forging, channel rolling, swaging, and wire drawing to form wires 1.0 and 0.8 mm in diameter. The rates of area reduction were about 30 to 90%. During the working, the works were process annealed in the temperature range of 400° to 900° C. and, after final working, finally annealed in the temperature range of 400° to 900° C. The average grain sizes were 2 to 150 μm.

The compositional analytical values of the titanium wire specimens thus obtained are listed in Table 4. The values for Specimens 1–20 in Table 4 are means of the values of 20 samples each. The compositional analytical values are given provided that the units digit of 5 and over was counted as ten and the units digit of 1 to 4 was cut away as zero.

As an alternative to the above process, each stock was rolled into a sheet, slit into square rods, with the corners rounded off with a grinder or the like, and then swaged and drawn into a wire in the same way as above. The wires so made showed practically no distinction in performance from the above specimens provided their compositional analytical values fell within the ranges specified by this invention.

As regards the annealing temperature ranges of 500° to 700° C. and 550° to 650° C. and also in the variations of the average grain size, the specimens whose values deviated from the "more desirable" or "preferable" numerical ranges tended to show somewhat more dispersions in properties than the specimens whose values were in those ranges. Those deviating specimens, however, displayed little differences in properties as long as their compositional analytical values came within the ranges of this invention.

For comparison purposes, titanium wires were made by the same manufacturing process and with the same compositional adjustments of the impurities.

The compositional analytical values of the comparative specimens are also listed in Table 4. The numerical values of Specimens 21 to 33 given in the table likewise are means of 20 samples. The numerical values of analysis again are given with the units digit of 5 and over was counted as ten and the units digit of 1 to 4 was cut away as zero.

TABLE 4

Changes in elongation and gap* with changes in impurities contents

|  |  | Ti | Fe | O | C | N | H | Impurities other than Fe & gaseous conts. | Elong. (%) | Proof stress (MPa) | Tens str (MPa) | Gap (mm) 0.8 | Gap (mm) 1.0 |
|---|---|---|---|---|---|---|---|---|---|---|---|---|---|
| Specimen in Example of this invention | 1 | bal. | 110 | 140 | 10 | 10 | <10 | <10 | 51.2 | 94.8 | 214.6 | 0.0 | 0.0 |
|  | 2 | bal. | 320 | 150 | 10 | 10 | <10 | <10 | 48.7 | 109.8 | 228.9 | 0.0 | 0.0 |
|  | 3 | bal. | 400 | 140 | 10 | 10 | <10 | <10 | 46.8 | 116.2 | 233.6 | 0.0 | 0.1 |
|  | 4 | bal. | 510 | 140 | 10 | 10 | <10 | <10 | 44.9 | 128.4 | 247.5 | 0.2 | 0.3 |
|  | 5 | bal. | 830 | 140 | 10 | 10 | <10 | <10 | 36.1 | 153.2 | 274.8 | 0.5 | 0.6 |
|  | 6 | bal. | 960 | 150 | 10 | 10 | <10 | <10 | 31.2 | 166.3 | 286.4 | 0.6 | 0.8 |
|  | 7 | bal. | 320 | 90 | 10 | 10 | <10 | <10 | 53.6 | 105.6 | 206.3 | 0.0 | 0.0 |
|  | 8 | bal. | 320 | 240 | 10 | 10 | <10 | <10 | 43.8 | 119.2 | 236.1 | 0.3 | 0.4 |
|  | 9 | bal. | 320 | 140 | 10 | 90 | <10 | <10 | 44.7 | 123.8 | 242.5 | 0.0 | 0.1 |
|  | 10 | bal. | 320 | 150 | 10 | 160 | <10 | <10 | 39.8 | 147.6 | 266.1 | 0.4 | 0.4 |
|  | 11 | bal. | 320 | 140 | 150 | 10 | <10 | <10 | 35.2 | 114.2 | 230.6 | 0.3 | 0.4 |
|  | 12 | bal. | 320 | 140 | 310 | 10 | <10 | <10 | 30.9 | 130.9 | 250.6 | 0.6 | 0.8 |
|  | 13 | bal. | 320 | 140 | 10 | 10 | 20 | <10 | 42.8 | 113.2 | 224.6 | 0.0 | 0.0 |
|  | 14 | bal. | 320 | 150 | 10 | 10 | 40 | <10 | 32.2 | 121.8 | 241.5 | 0.7 | 0.6 |
|  | 15 | bal. | 320 | 150 | 10 | 10 | <10 | 30 | 46.7 | 112.4 | 243.1 | 0.0 | 0.0 |
|  | 16 | bal. | 320 | 140 | 10 | 10 | <10 | 70 | 32.8 | 146.3 | 267.3 | 0.7 | 0.7 |
|  | 17 | bal. | 200 | 140 | 60 | 80 | <10 | <10 | 48.9 | 124.8 | 245.2 | 0.0 | 0.0 |
|  | 19 | bal. | 460 | 170 | 140 | 110 | 20 | 20 | 42.1 | 138.0 | 266.3 | 0.1 | 0.1 |
|  | 20 | bal. | 750 | 210 | 280 | 150 | 50 | 50 | 32.4 | 152.7 | 277.8 | 0.5 | 0.4 |
| Specimen of Comparative Example | 21 | bal. | 1100 | 140 | 10 | 10 | <10 | <10 | 26.5 | 182.3 | 293.1 | 2.2 | 2.3 |
|  | 22 | bal. | 1210 | 140 | 20 | 10 | <10 | <10 | 25.8 | 189.2 | 299.6 | 2.5 | 2.6 |
|  | 23 | bal. | 1480 | 150 | 10 | 10 | <10 | <10 | 19.1 | 212.1 | 331.2 | 4.2 | 3.9 |
|  | 24 | bal. | 320 | 320 | 10 | 10 | <10 | <10 | 27.6 | 128.7 | 240.1 | 1.4 | 1.6 |
|  | 25 | bal. | 320 | 460 | 10 | 10 | <10 | <10 | 21.2 | 142.6 | 251.6 | 1.6 | 1.7 |
|  | 26 | bal. | 320 | 150 | 10 | 210 | <10 | <10 | 24.8 | 167.3 | 288.3 | 2.4 | 2.6 |
|  | 27 | bal. | 320 | 140 | 10 | 260 | <10 | <10 | 22.1 | 172.1 | 296.5 | 2.8 | 2.7 |
|  | 28 | bal. | 320 | 140 | 420 | 10 | <10 | <10 | 24.1 | 135.0 | 254.9 | 2.3 | 2.5 |
|  | 29 | bal. | 320 | 140 | 480 | 10 | <10 | <10 | 23.5 | 155.2 | 274.4 | 2.7 | 2.7 |
|  | 30 | bal. | 320 | 140 | 10 | 10 | 60 | <10 | 21.4 | 148.1 | 267.5 | 2.6 | 2.7 |
|  | 31 | bal. | 320 | 140 | 10 | 10 | 70 | <10 | 17.3 | 155.3 | 271.5 | 3.8 | 4.5 |
|  | 32 | bal. | 320 | 150 | 10 | 10 | <10 | 120 | 27.8 | 165.0 | 280.3 | 3.9 | 4.3 |
|  | 33 | bal. | 320 | 140 | 10 | 10 | <10 | 160 | 27.6 | 178.6 | 296.1 | 4.5 | 4.7 |

Figure 19:
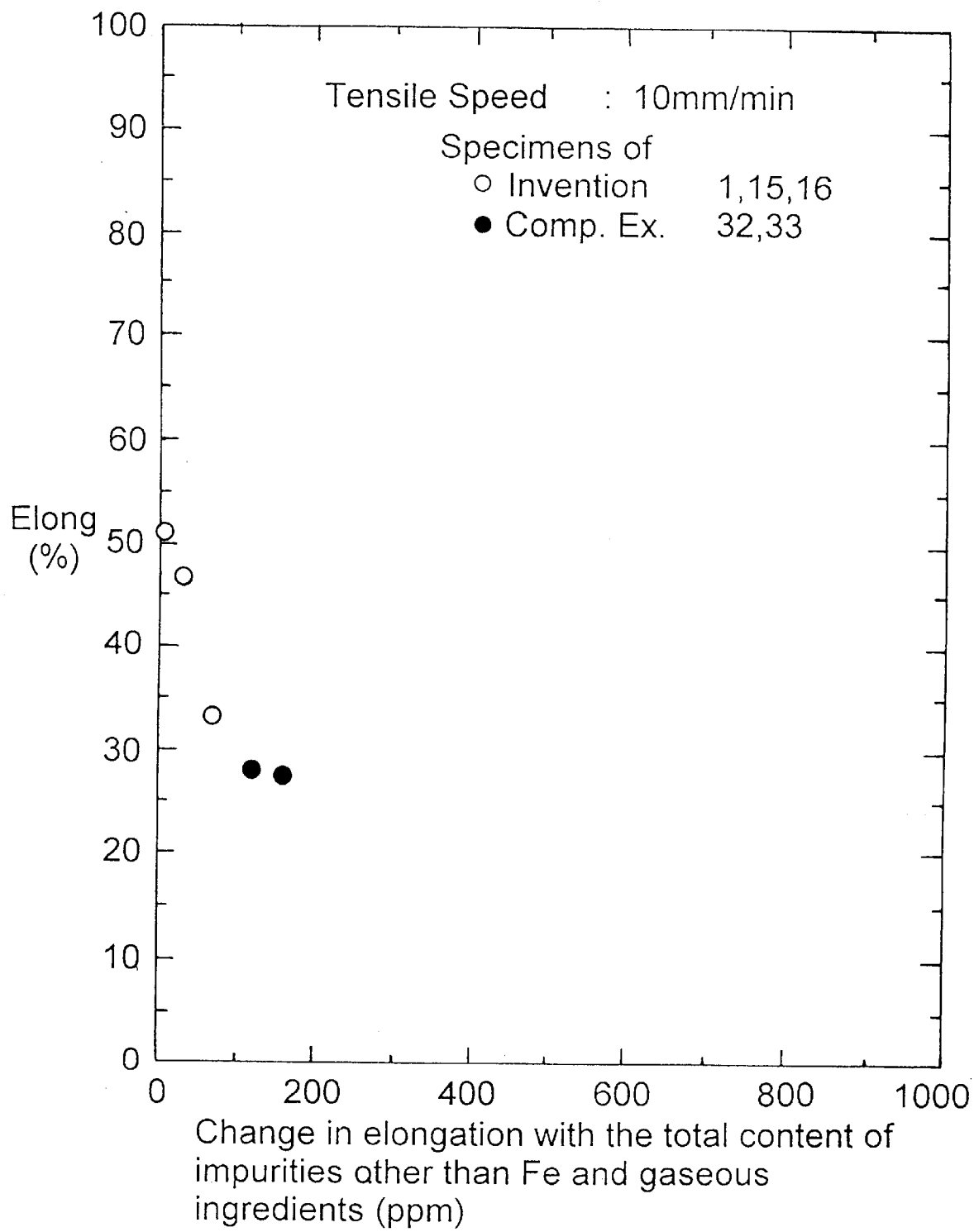
FIG. 19 is a graph showing changes in elongation with the contents of impurities other than iron and the gaseous ingredients in Example 4 and Comparative Example 4.

*Refer to FIG. 19,
Speed: 60 rpm

Next, these specimens were subjected to the following tests.
(1) Tensile Test (Measurement of Elongation, and Determination of Proof Stress and Tensile Strength)
Two wires with different gage diameters were tested for tensile strength.
Length between gage marks : 70 mm
Tensile testing speed: 10 mm/min
Gage diameters: 1.0 and 0.8 mm
(2) Twist Test
Each set of two wires with different diameters were subjected to a twist test.
Jig as object of winding: rounded bar-fixing jig 20 mm in diameter
Rotational speed: 60 rpm
Wire diameters: 1.0 and 0.8 mm
The results of measurements of elongation made by the tensile tests are shown in Table 4 and FIGS. 14 to 19.

As will be clear from Table 4, Specimens 1 to 20 in Example of this invention, without exception, had good ductility with elongation values of more than 30%. The ductility was high, even when a predetermined amount of iron was contained, especially when the amounts of the gaseous ingredients they contained were: 200 ppm or less oxygen, 30 ppm or less hydrogen, 100 ppm or less nitrogen, 100 ppm or less carbon, and 50 ppm or less impurities other than the gaseous ingredients and iron. More preferable ranges were 150 ppm or less oxygen, 20 ppm or less hydrogen, 20 ppm or less nitrogen, 50 ppm or less carbon, and 20 ppm or less impurities other than the gaseous ingredients and iron. With the latter ranges, extremely high ductility is attained.

In contrast to these, it will be seen that all of Specimens 21 to 33 presented as Comparative Example were quite inferior in ductility, with elongation values of less than 30%. None of Specimens 20 to 30 are suitable as titanium fixation wires for the living body, since the compositions of the comparative specimens exceeds 1000 ppm iron, or exceeds one or more of 1000 ppm iron, 300 ppm oxygen, 50 ppm hydrogen, 200 ppm nitrogen, 400 ppm carbon, and 100 ppm impurities other than the gaseous ingredients and iron.

Figure 14:
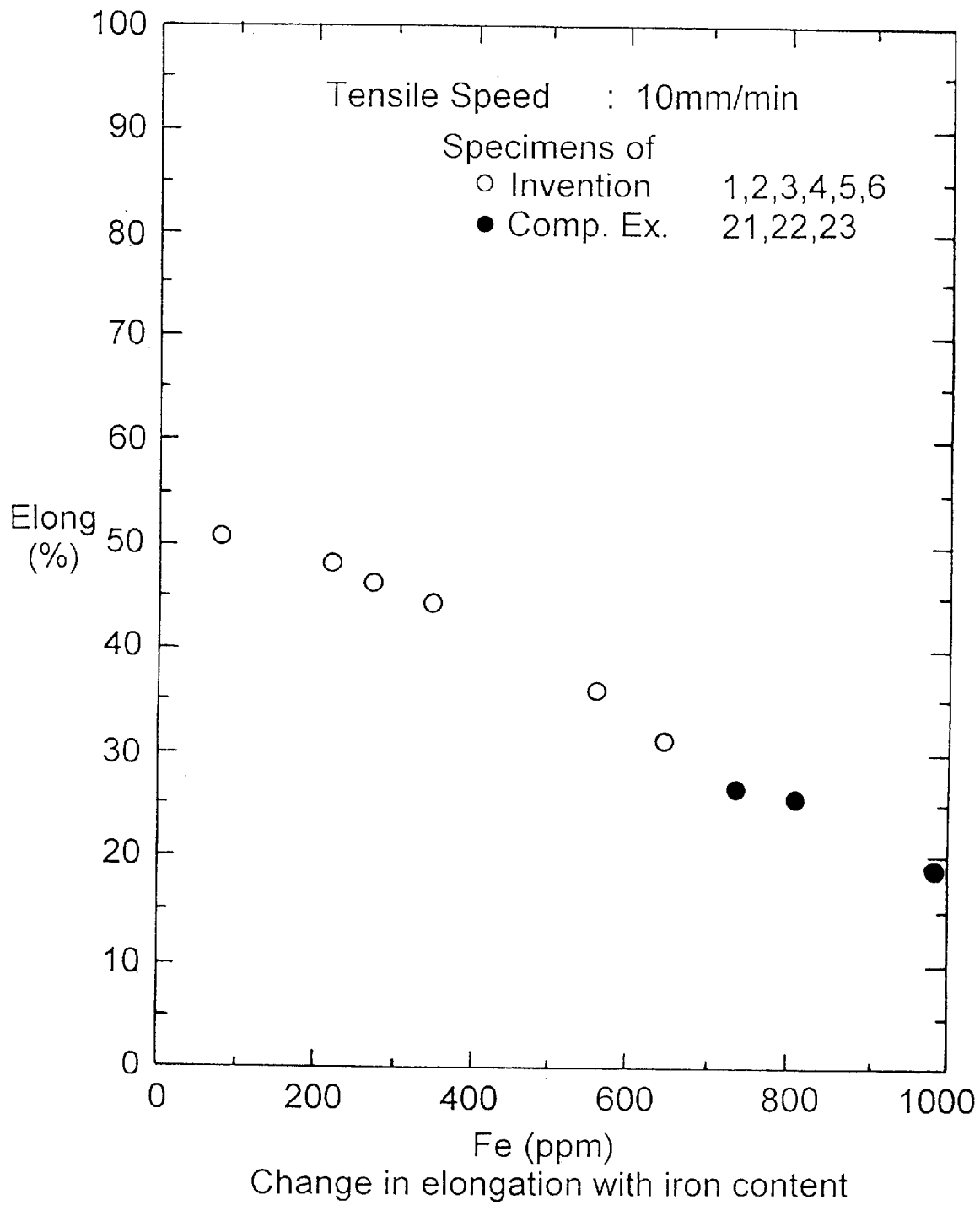
FIG. 14 is a graph showing changes in elongation with the iron contents in Example 4 and Comparative Example 4.

FIG. 14 shows changes in elongation with the iron contents of Specimens 1 to 6 in Example of this invention and of Specimens 21 to 23 of Comparative Example.

Figure 15:
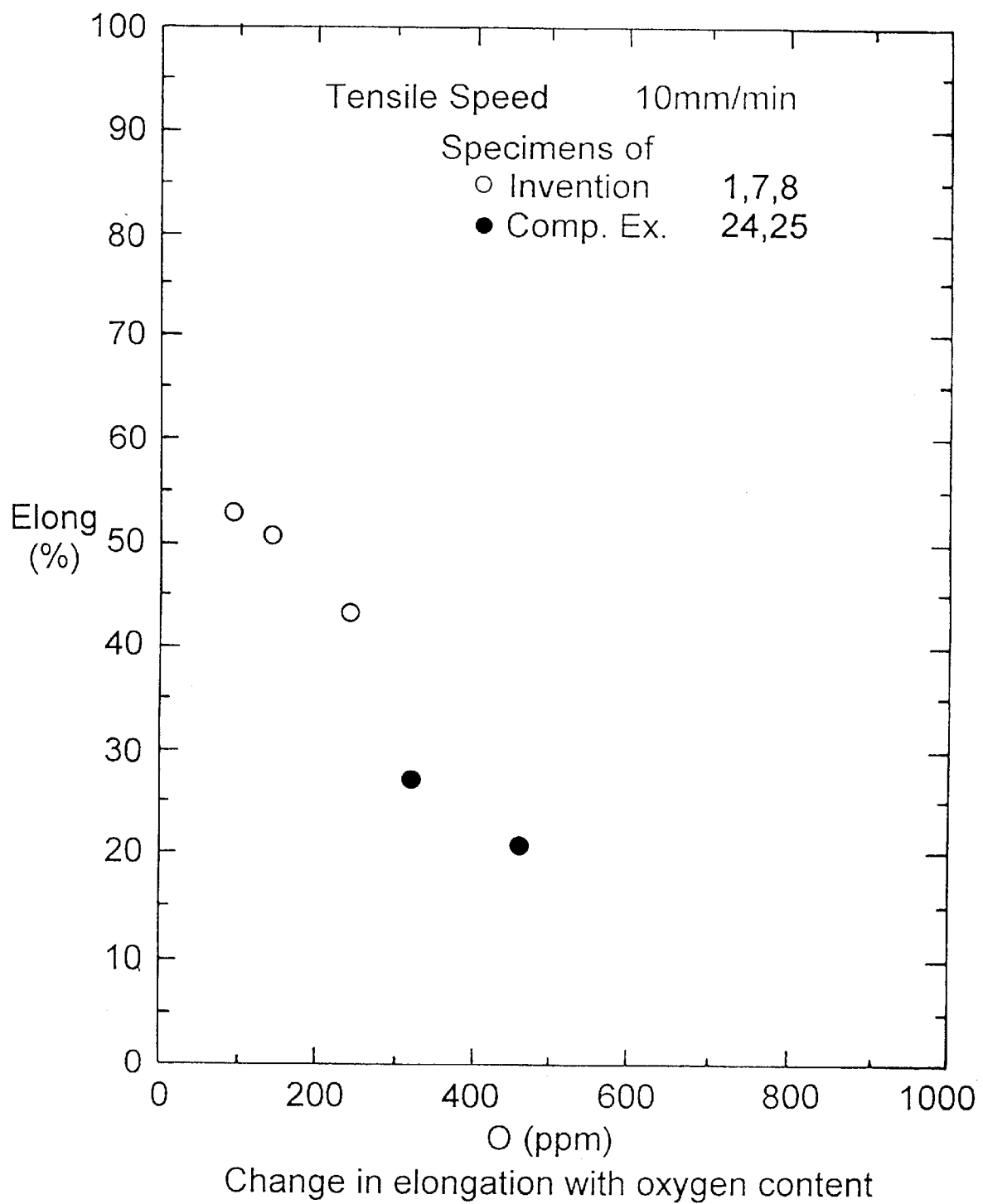
FIG. 15 is a graph showing changes in elongation with the oxygen contents in Example 4 and Comparative Example 4.

FIG. 15 shows changes in elongation with the oxygen contents of Specimens 1, 7, and 8 and of Specimens 24 and 25 of Comparative Example.

Figure 16:
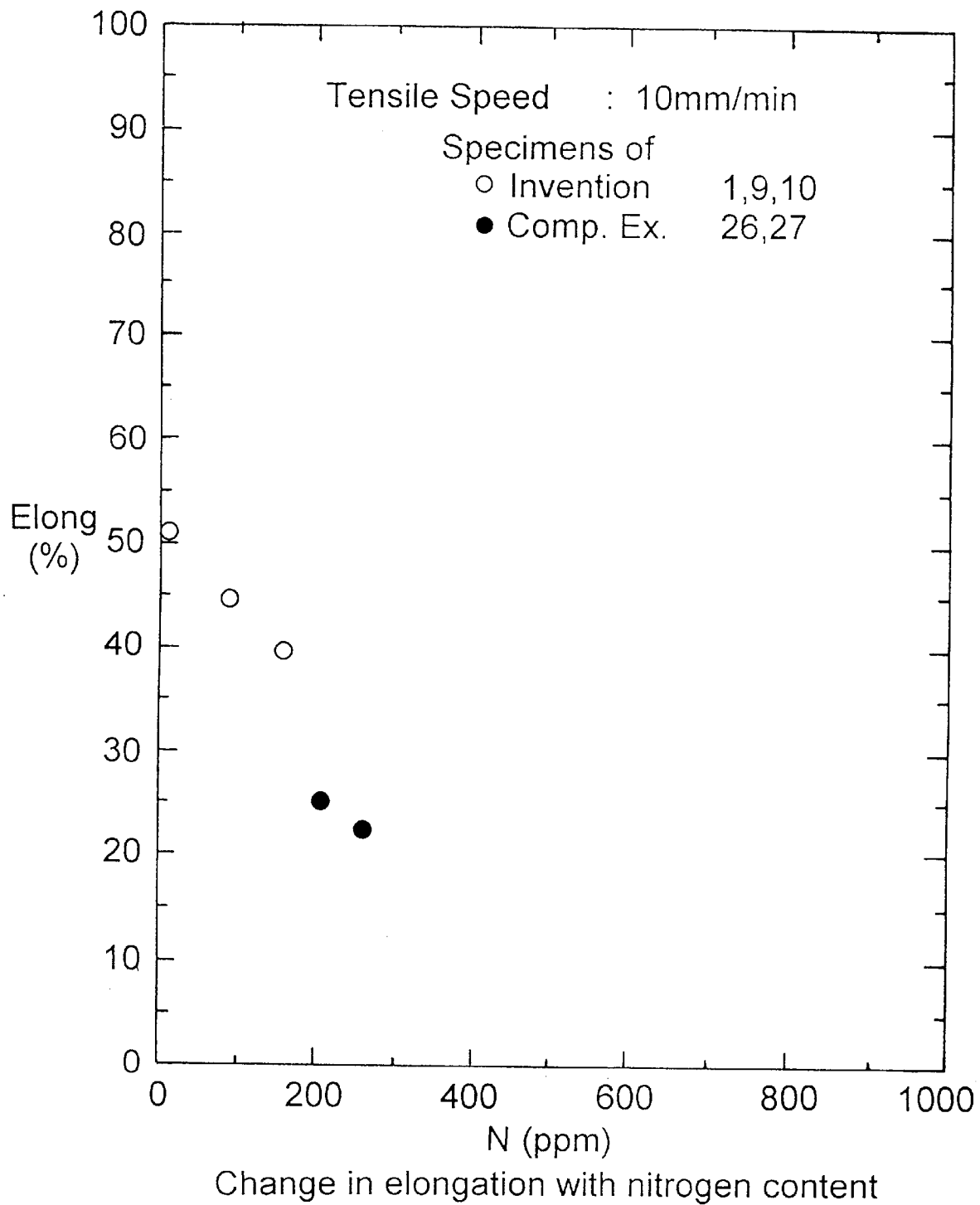
FIG. 16 is a graph showing changes in elongation with the nitrogen contents in Example 4 and Comparative Example 4.

FIG. 16 shows changes in elongation with the nitrogen contents of Specimens 1, 9, and 10 and of Specimens 26 and 27 of Comparative Example.

Figure 17:
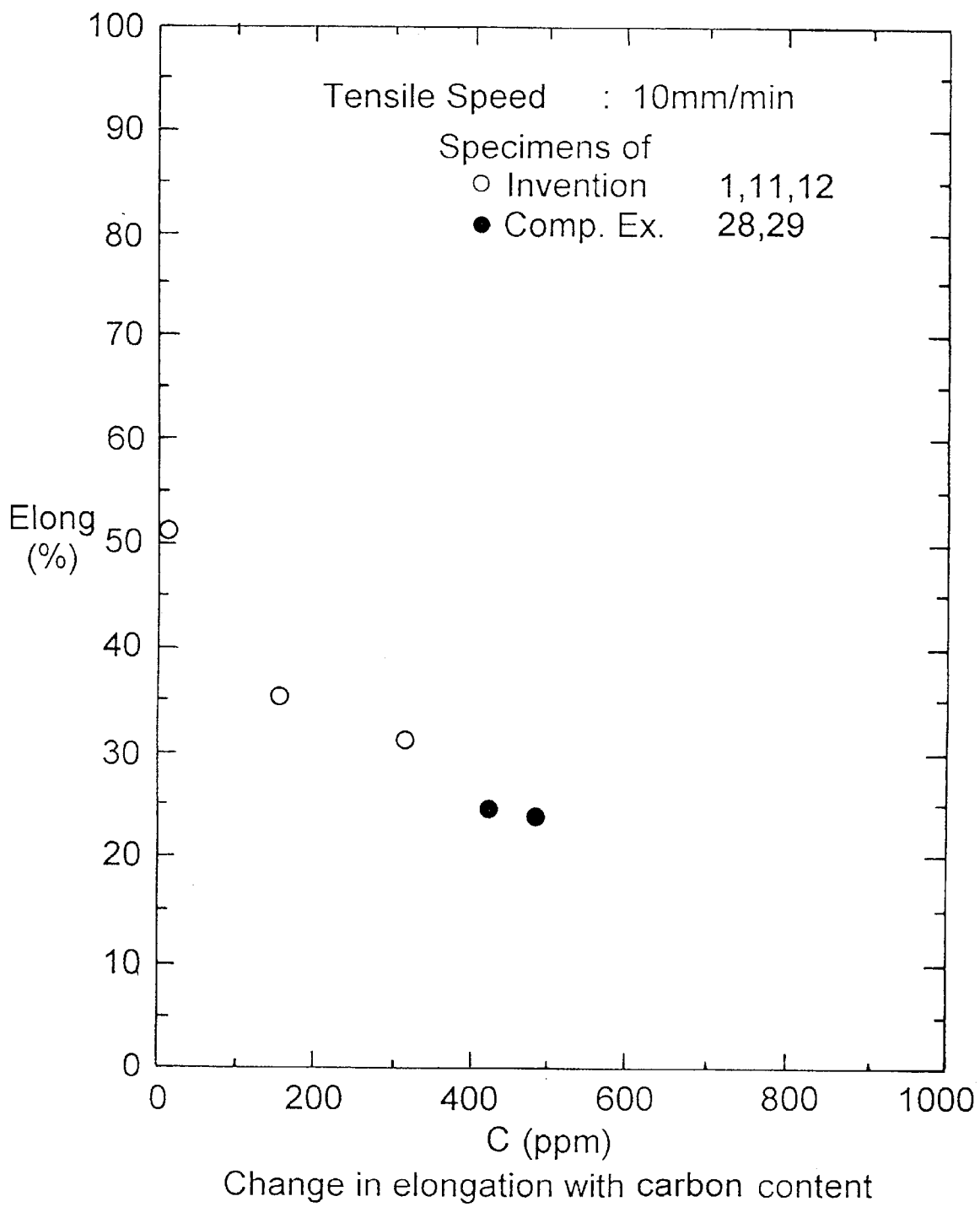
FIG. 17 is a graph showing changes in elongation with the carbon contents in Example 4 and Comparative Example 4.

FIG. 17 shows changes in elongation with the carbon contents of Specimens 1, 11, and 12 and of Specimens 28 and 29 of Comparative Example.

Figure 18:
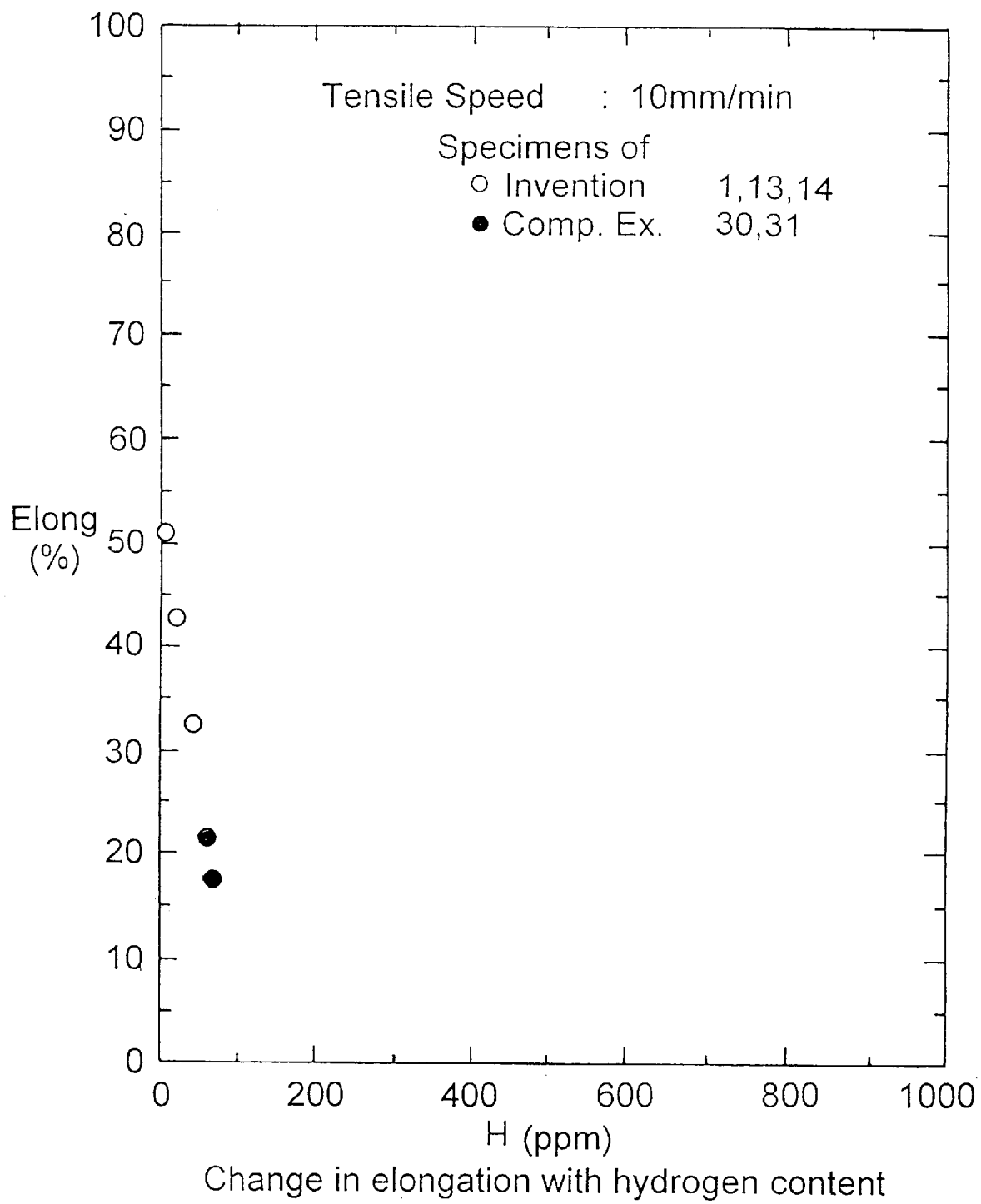
FIG. 18 is a graph showing changes in elongation with the hydrogen contents in Example 4 and Comparative Example 4.

FIG. 18 shows changes in elongation with the hydrogen contents of Specimens 1, 13 and 14 and of Specimens 30 and 31 of Comparative Example.

FIG. 19 shows changes in elongation with the amounts of impurities other than iron and the gaseous ingredients contained in Specimens 1, 15, and 16 and in Specimens 32 and 33 of Comparative Example. It is quite clear that the specimens of the invention exhibit better elongation than the comparative specimens.

As for the tensile strength and proof stress as measured in the tensile tests, they gave values of more than 175 MPa and 70 MPa, respectively, and, without practical drawbacks, they were suitable as fixation wires for the living body.

The results of proof stress and tensile strength measurements by tensile tests are shown in Table 4 and FIGS. 20 to 25. As will be appreciated from Table 4, Specimens 1 to 20 in Example of this invention displayed good strength with proof stress values of more than 70 MPa and tensile strength values of more than 175 MPa. Especially with an iron content of more than 300 ppm, the proof stress was more than 200 MPa and the tensile strength was more than 200 MPa, indicating a marked improvement in strength. Additionally remarkable are an only limited decrease in ductility and the ability of binding with practically no gap as will be evidenced in twist tests to be described later. As the iron content exceeds 400 ppm, both the proof stress and tensile strength continue to increase and yet the decrease in ductility is again rather negligible.

Figure 20:
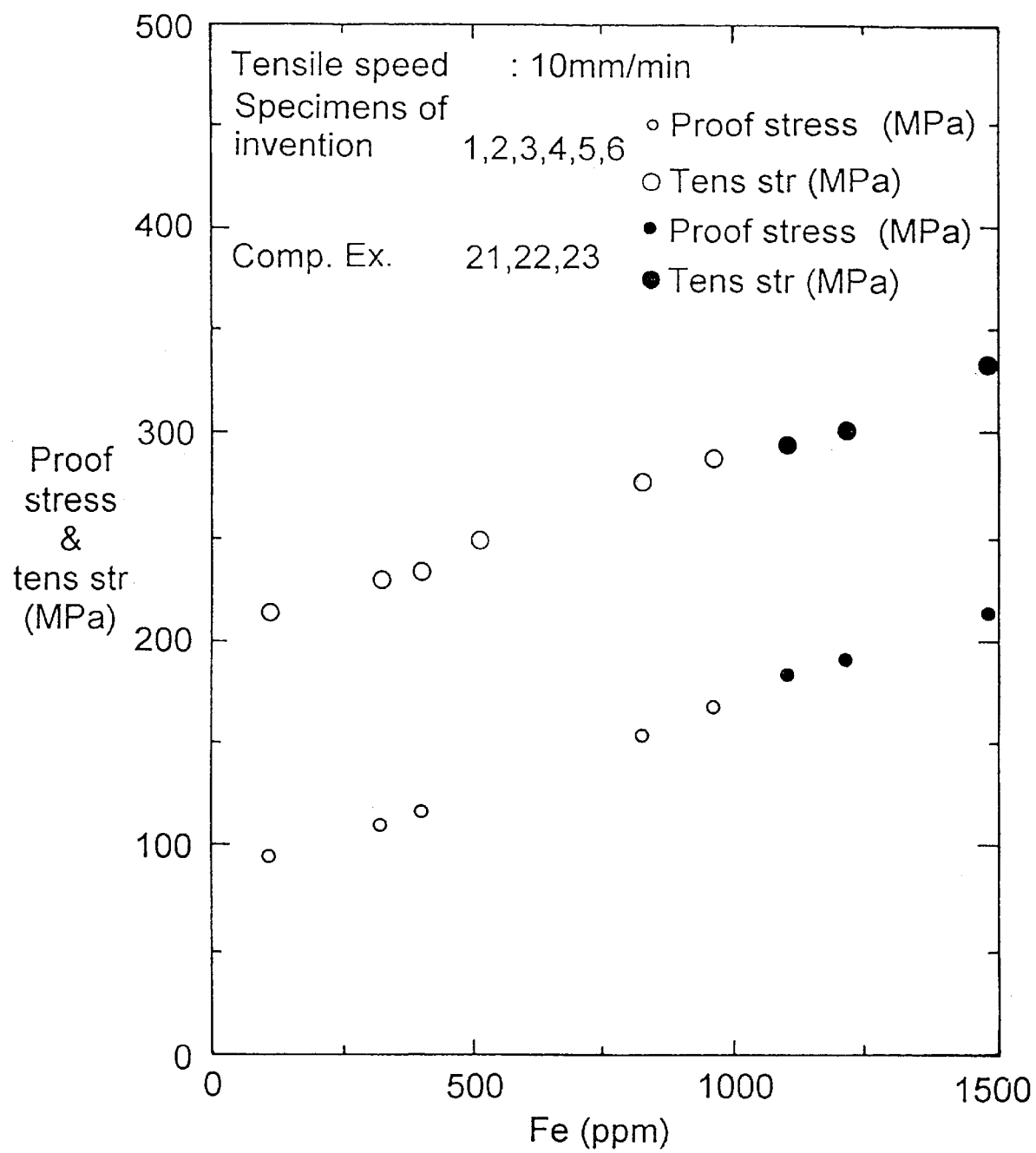
FIG. 20 is a graph showing changes in proof stress and tensile strength with the iron contents in Example 4 and Comparative Example 4.

FIG. 20 shows changes in proof stress and tensile strength with the iron contents of Specimens 1 to 6 according to this invention and of Specimens 21, 22 and 23 of Comparative Example.

Figure 21:
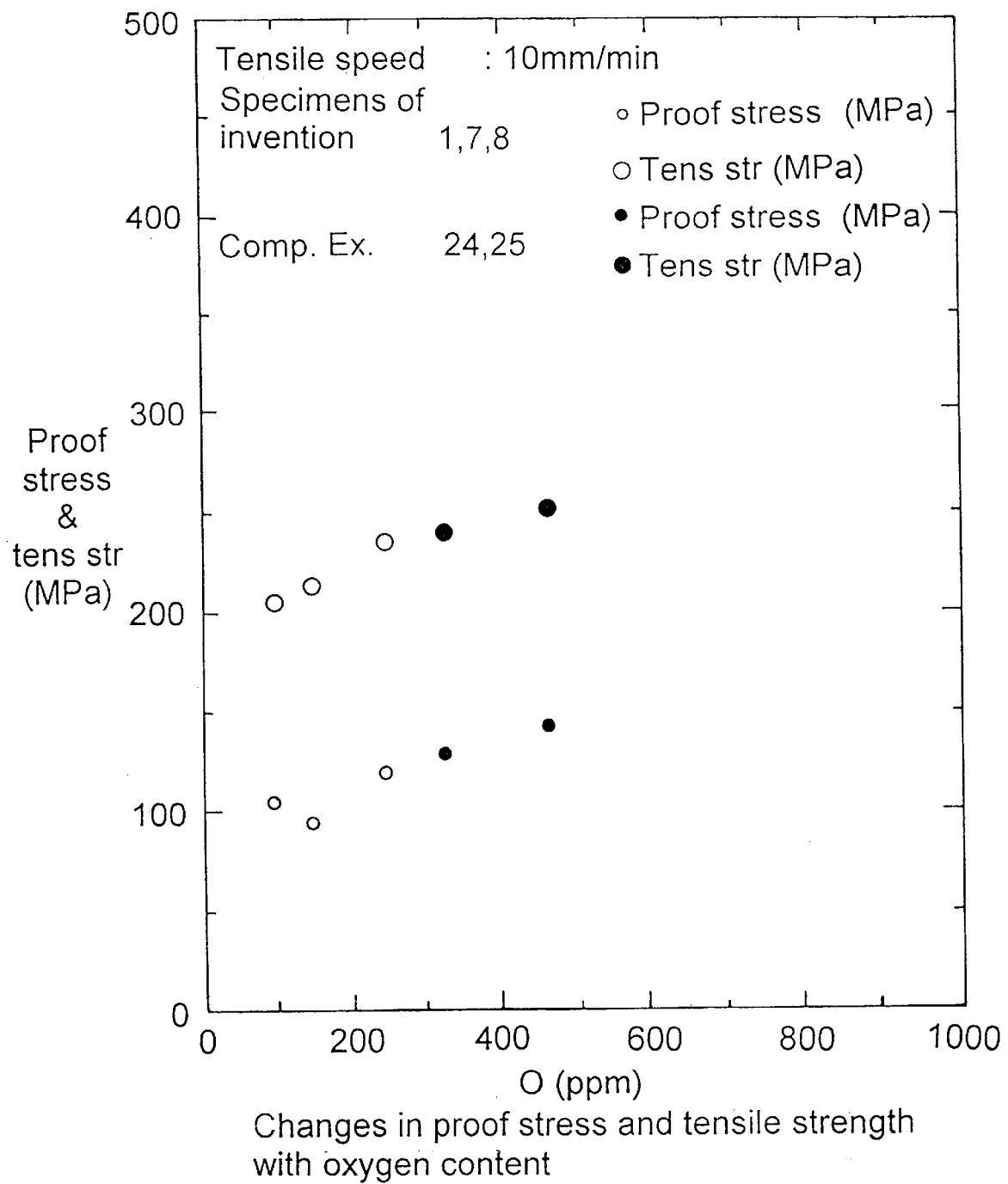
FIG. 21 is a graph showing changes in proof stress and tensile strength with the oxygen contents in Example 4 and Comparative Example 4.

FIG. 21 shows changes in proof stress and tensile strength with the oxygen contents of Specimens 1, 7, and 8 according to this invention and of Specimens 24 and 25 of Comparative Example.

Figure 22:
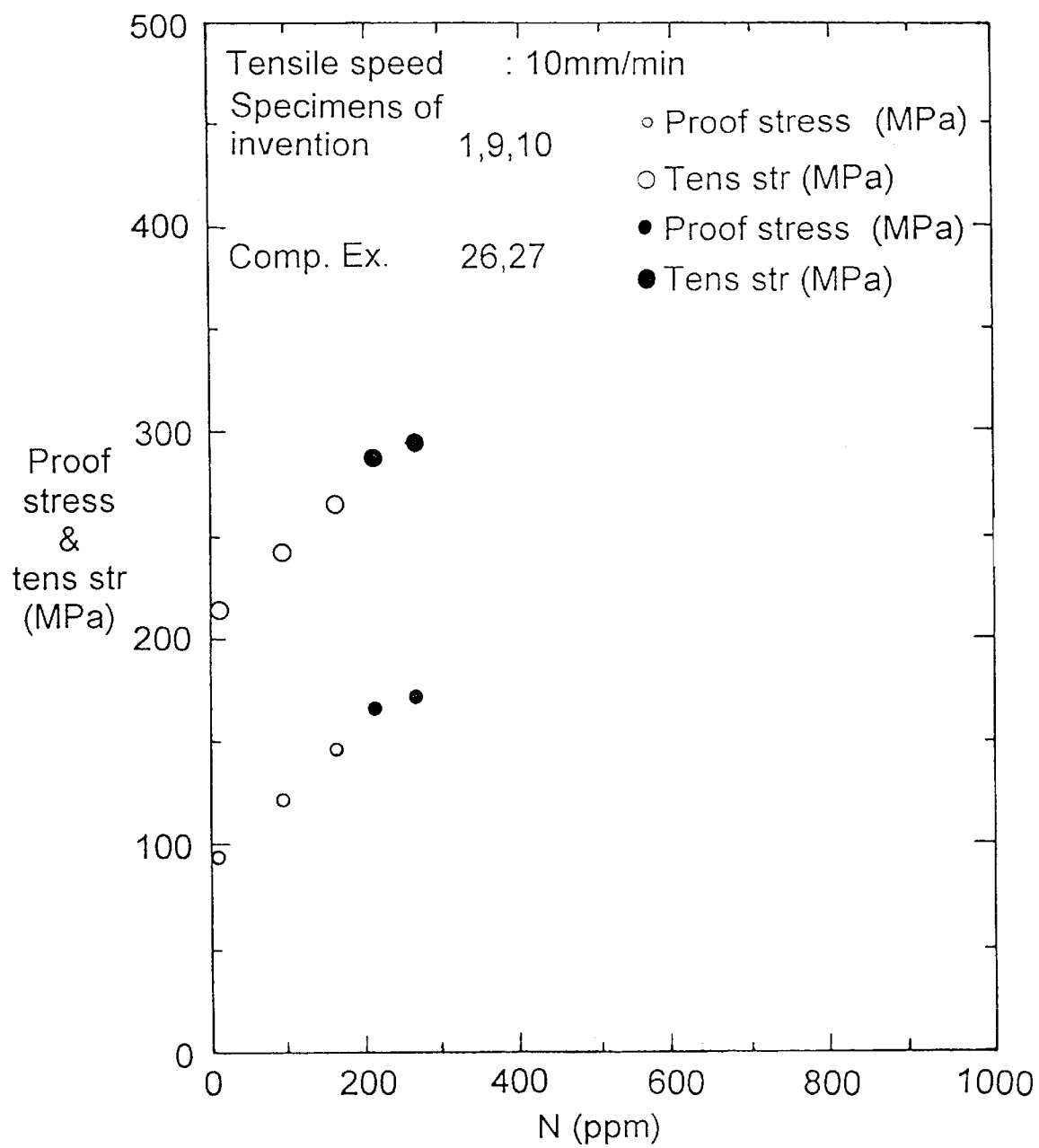
FIG. 22 is a graph showing changes in proof stress and tensile strength with the nitrogen contents in Example 4 and Comparative Example 4.

FIG. 22 shows changes in proof stress and tensile strength with the nitrogen contents of Specimens 1, 9, and 10 according to this invention and of Specimens 26 and 27 of Comparative Example.

Figure 23:
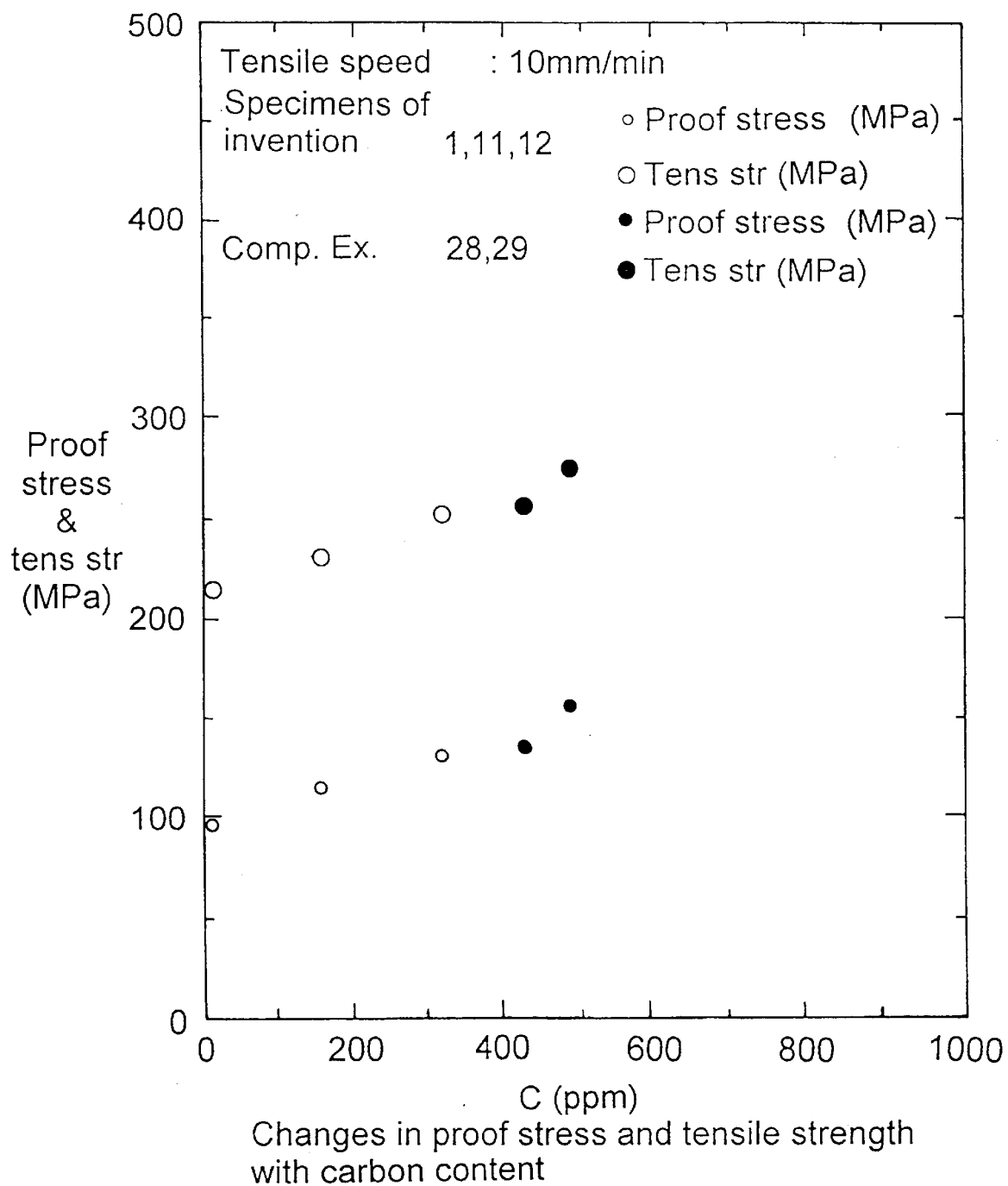
FIG. 23 is a graph showing changes in proof stress and tensile strength with the carbon contents in Example 4 and Comparative Example 4.

FIG. 23 shows changes in proof stress and tensile strength with the carbon contents of Specimens 1, 11, and 12 according to this invention and of Specimens 28 and 29 of Comparative Example.

Figure 24:
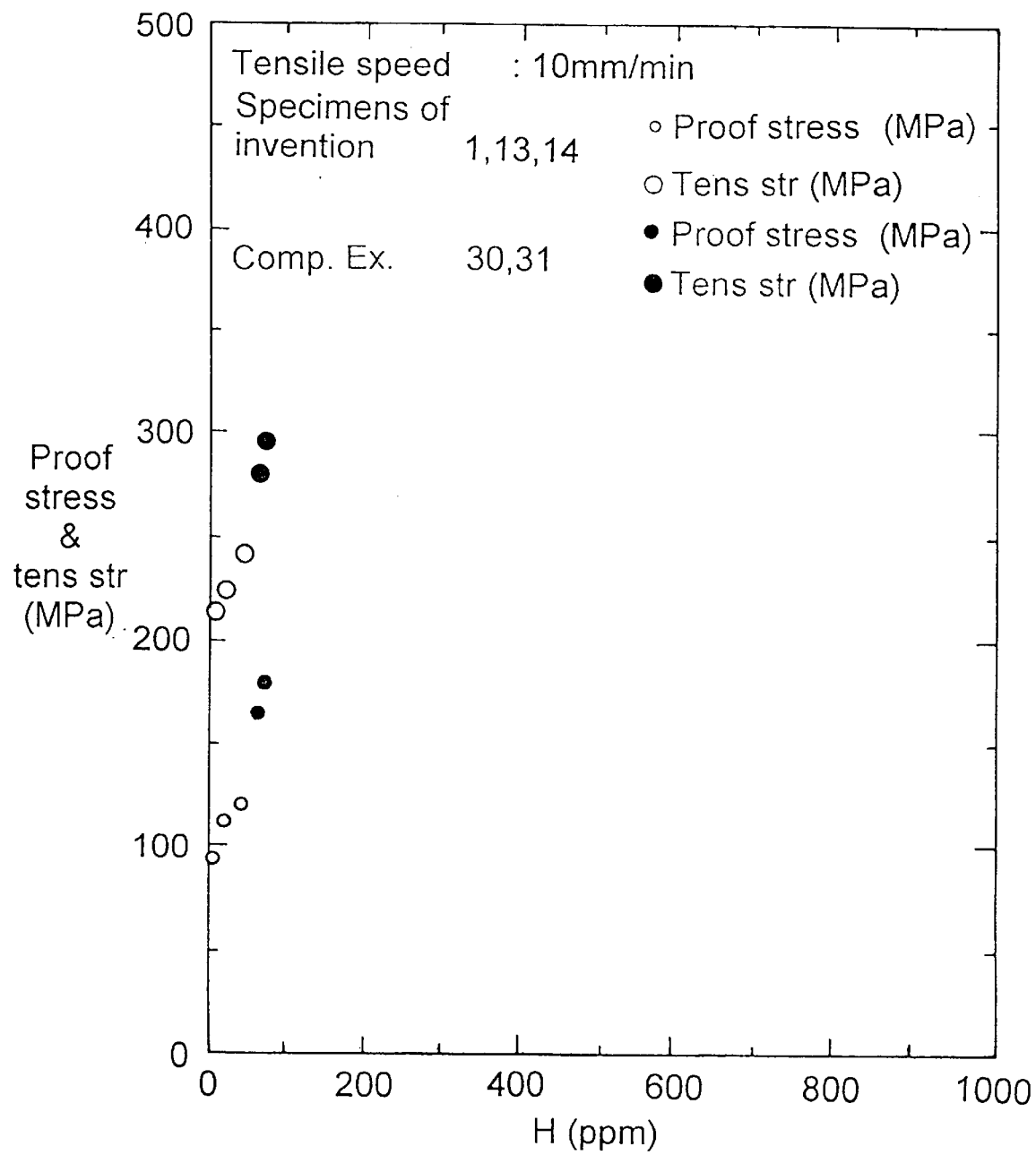
FIG. 24 is a graph showing changes in proof stress and tensile strength with the hydrogen contents in Example 4 and Comparative Example 4.

FIG. 24 shows changes in proof stress and tensile strength with the hydrogen contents of Specimens 1, 13, and 14 according to this invention and of Specimens 30 and 31 of Comparative Example.

Figure 25:
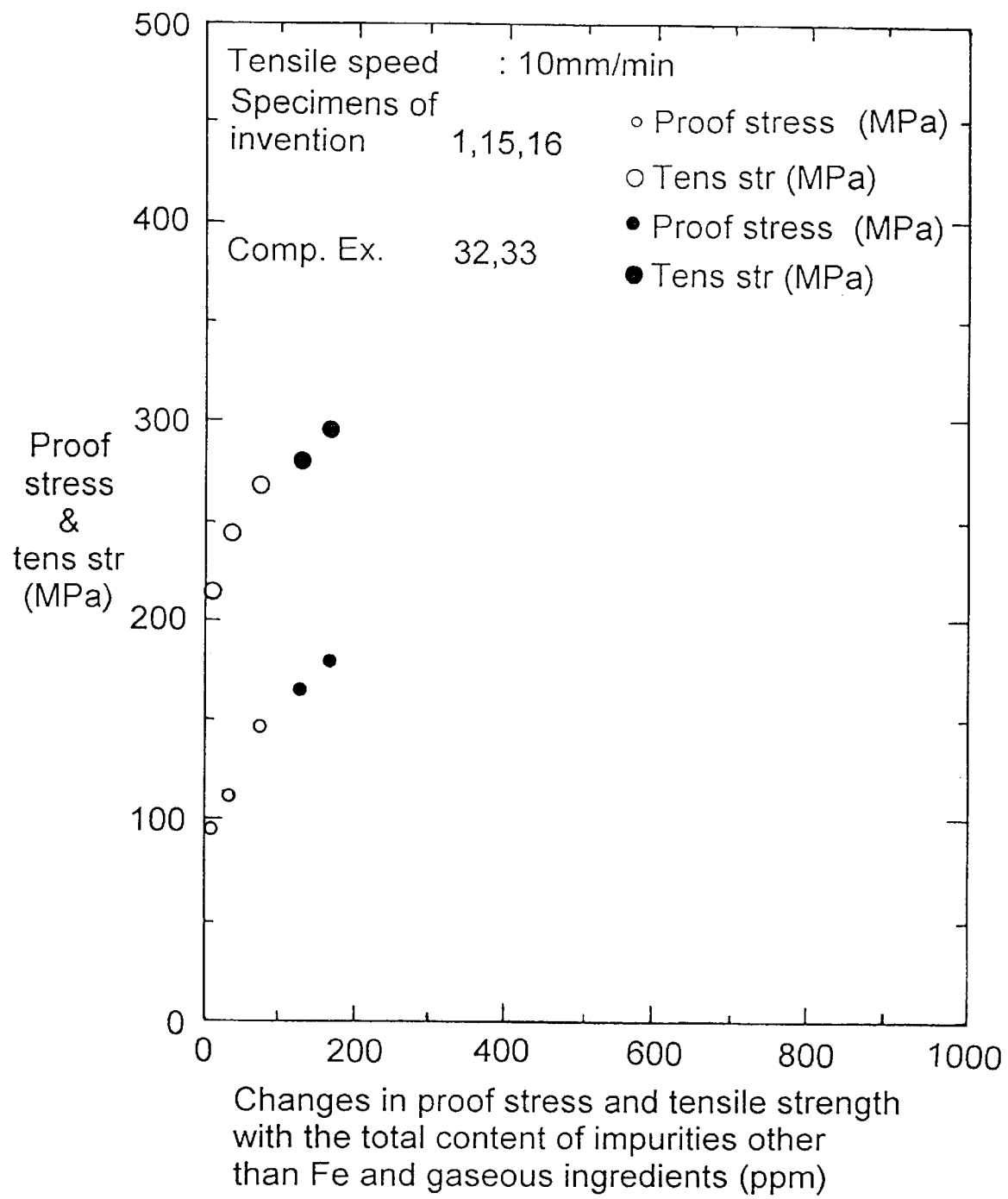
FIG. 25 is a graph showing changes in proof stress and tensile strength with the contents of impurities other than iron and the gaseous ingredients in Example 4 and Comparative Example 4.
Figure 26:
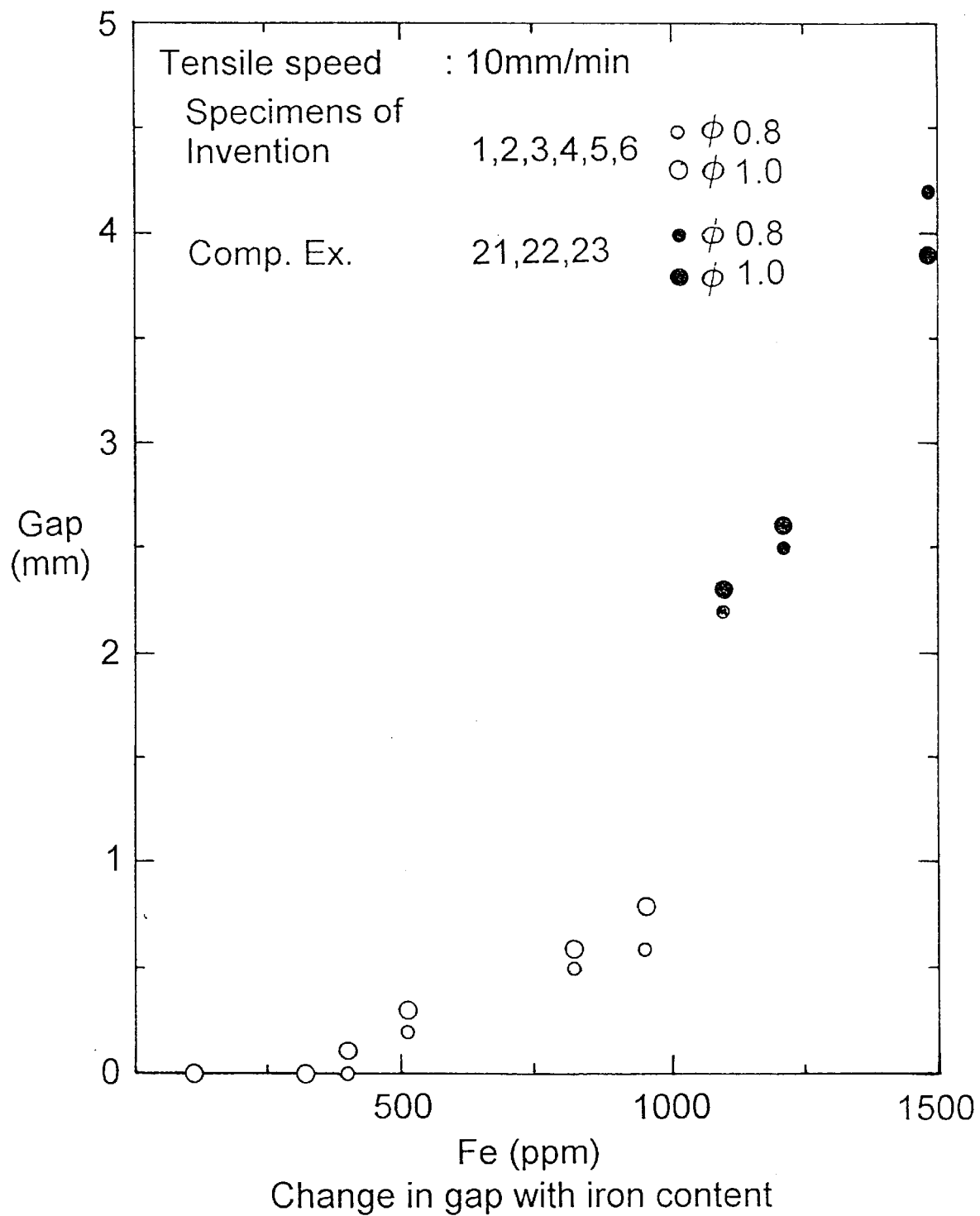
FIG. 26 is a graph showing changes in gap with the iron contents in Example 4 and Comparative Example 4.
Figure 27:
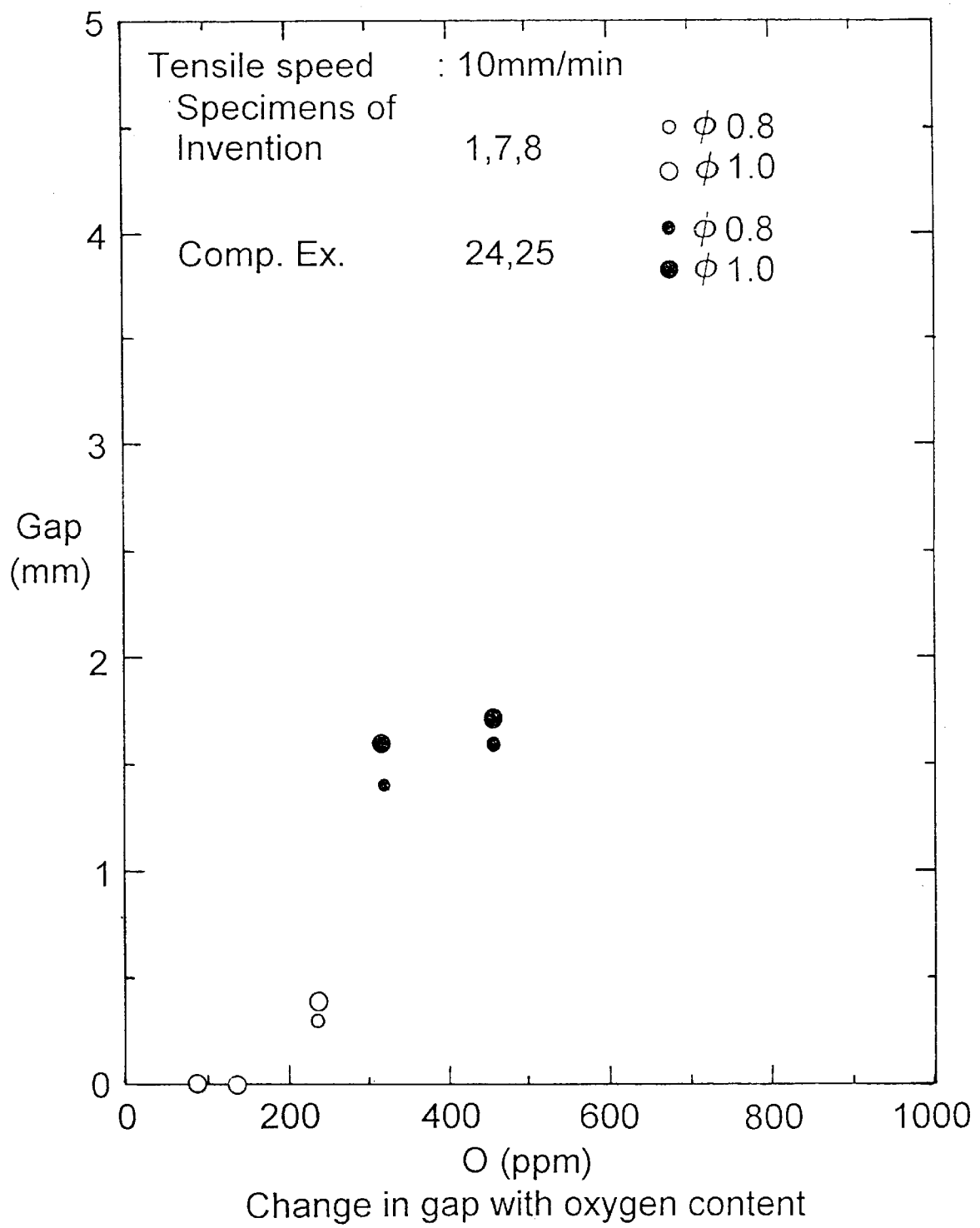
FIG. 27 is a graph showing changes in gap with the oxygen contents in Example 4 and Comparative Example 4.
Figure 28:
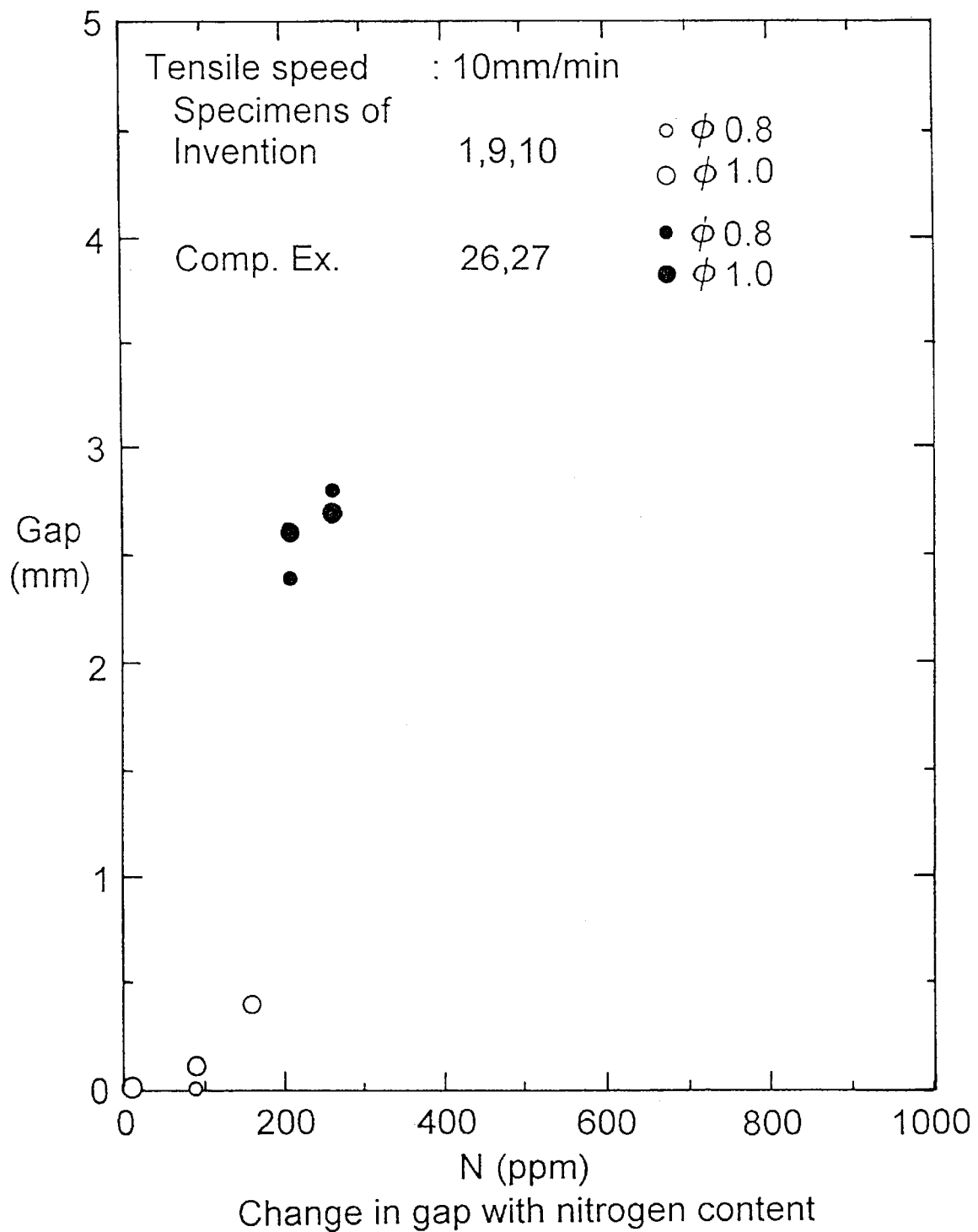
FIG. 28 is a graph showing changes in gap with the nitrogen contents in Example 4 and Comparative Example 4.
Figure 29:
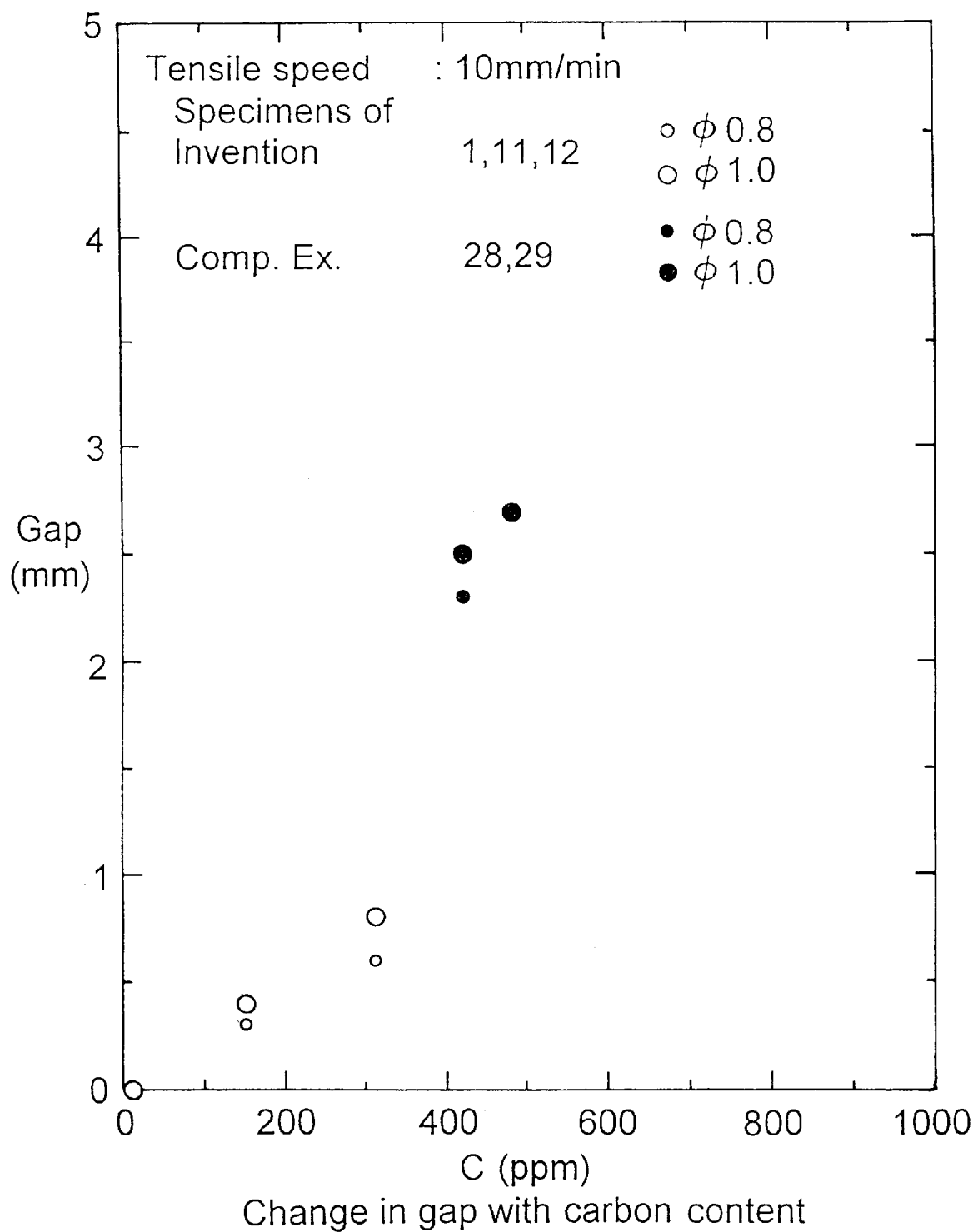
FIG. 29 is a graph showing changes in gap with the carbon contents in Example 4 and Comparative Example 4.
Figure 30:
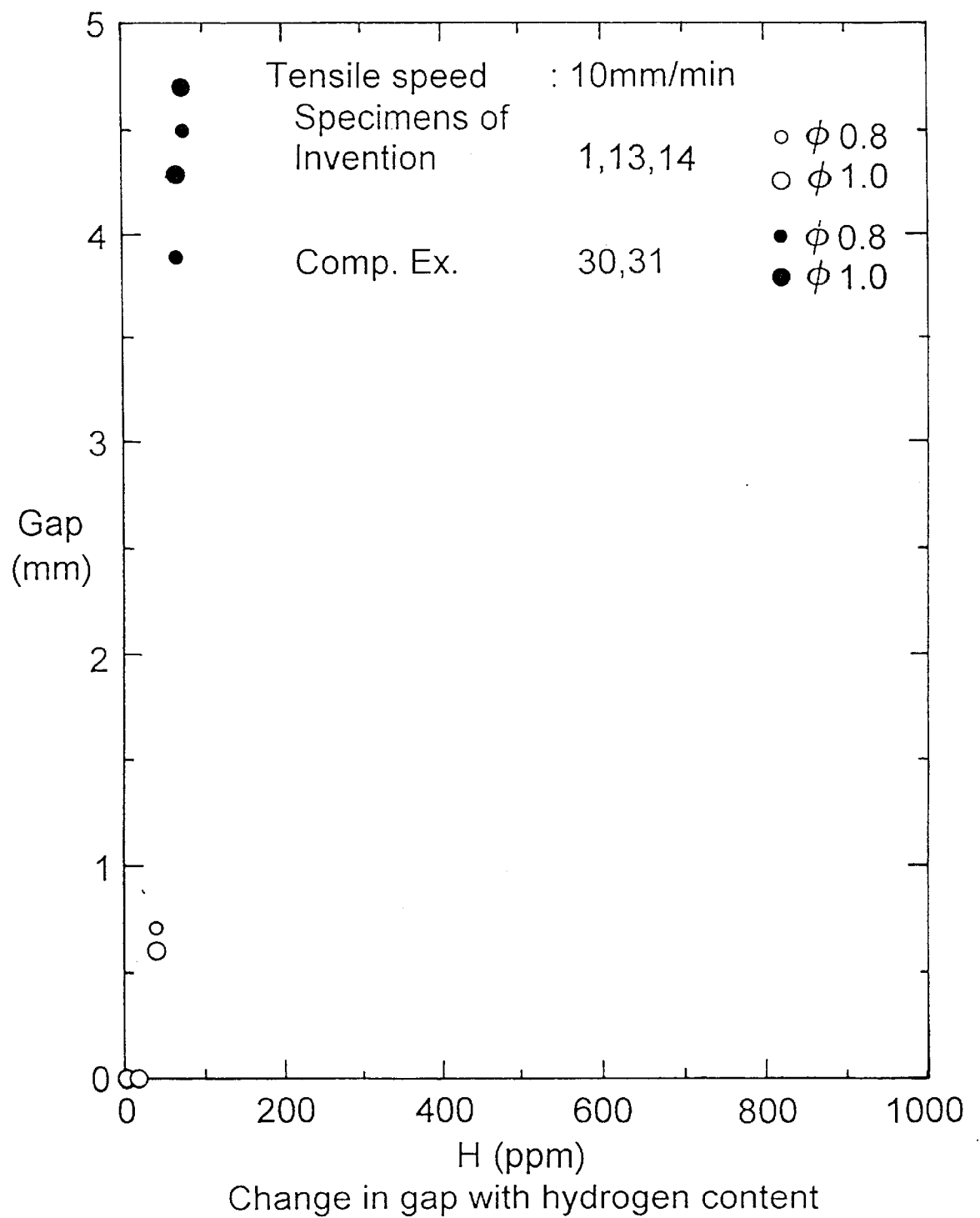
FIG. 30 is a graph showing changes in gap with the hydrogen contents in Example 4 and Comparative Example 4.
Figure 31:
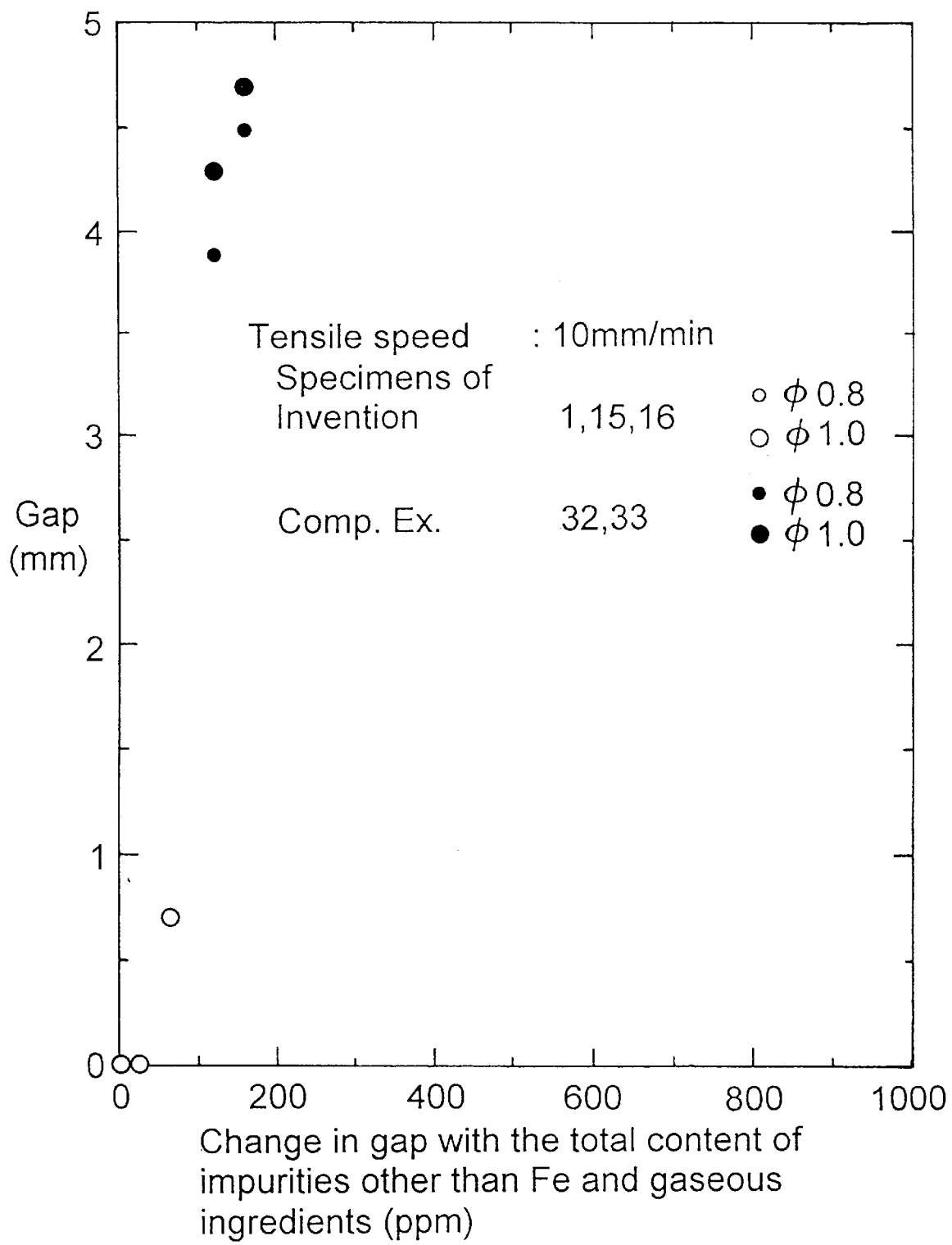
FIG. 31 is a graph showing changes in gap with the contents of impurities other than iron and the gaseous ingredients in Example 4 and Comparative Example 4.

FIG. 25 shows changes in proof stress and tensile strength with the impurities other than iron and the gaseous ingredients contained in Specimens 1, 15, and 16 according to this invention and in Specimens 32 and 33 of Comparative Example.

The Example of the present invention and Comparative Example thus far described indicate that both the proof stress and tensile strength of the materials increase generally in direct proportion to the amounts of various ingredients contained. However, excessive contents can cause sharp decreases in ductility, and it is important that those ingredients be contained in amounts specified by this invention.

The results of twist tests are shown in Table 4 and 5 and in FIGS. 26 through 31, and the patterns of breaks are based on ones as illustrated in FIG. 13.

TABLE 5

| | Patterns* of break in torsion tests | | |
|---|---|---|---|
| | | φ 0.8 | φ 1.0 |
| Specimen in | 1 | A | A |
| Example of | 2 | A | A |

TABLE 5-continued

| | Patterns* of break in torsion tests | | |
|---|---|---|---|
| | | φ 0.8 | φ 1.0 |
| this | 3 | A | A |
| invention | 4 | A | A |
| | 5 | A | A |
| | 6 | A | A |
| | 7 | A | A |
| | 8 | A | A |
| | 9 | A | A |
| | 10 | A | A |
| | 11 | A | A |
| | 12 | A | A |
| | 13 | A | A |
| | 14 | A | A |
| | 15 | A | A |
| | 16 | A | A |
| | 17 | A | A |
| | 18 | A | A |
| | 19 | A | A |
| | 20 | A | A |
| Specimen of | 21 | B | B |
| Comparative | 22 | B | C |
| Example | 23 | C | C |
| | 24 | B | B |
| | 25 | B | B |
| | 26 | B | B |
| | 27 | B | B |
| | 28 | B | B |
| | 29 | B | B |
| | 30 | B | B |
| | 31 | B | C |
| | 32 | B | B |
| | 33 | C | C |

Speed: 60 rpm
*Classified by Types A, B, and C as follows: (Refer to FIG. 13.)
Gap
A < 1.0
B ≥ 1.0
C = broken at a transition point between a twist and a straight line portion.

As already explained in FIG. 13, in twist tests, wires are wound around bar-fixing jigs 20 mm in diameter each at a speed of 60 rpm. Type A represents a break pattern of a wire tightly wound around the jig and twisted up to the binding end on the object with little gap (less than 1.0 mm) in between. When the wire breaks (due to overtwisting), the break occurs midway the twisted portion, where the working strains are concentrated. This represents a favorable pattern of break.

In Type B the wire breaks while it is unable to be wound completely and twisted up to the binding end on the jig (with a gap of more than 1.0 mm). This results from inadequate ductility of the wire. In this case slackening can take place in the bind.

In Type C a break occurs at a transition point between the twisted portion and the single wire (element) portion. The fixation wire in this state is utterly inadequate.

As is obvious from Table 5, Specimens 1 to 20 embodying this invention, with both diameters of 1.0 and 0.8 mm, showed break patterns of Type A, indicating that they were fitly wound round the jigs, twisted up to the binding end on the objects with little gaps (less than 1.0 mm) in between.

The particulars of gaps formed by wires in winding around jigs are shown in Table 4 and FIGS. 26 through 31. Specimens 1 to 20 left gaps of less than 1.0 mm, indicating that the higher the ductility the better. Some specimens could be twisted up to the wire-binding end on the jigs closely enough to leave no gap in between.

Specimens 21 to 33 of Comparative Example, by contrast, broke in the patterns of either Type B or C. As Table 4 and FIGS. 26 to 32 illustrate, the wires broke before they were twisted up to the binding ends on jigs (leaving a gap of more than 1.0 mm) or broke at a transition point between the twisted and single wire (element) portions. While proof stress and tensile strength are, of course, requisites for titanium fixation wires, a substantial slack in binding or a break before the completion of binding of the wires can be fatal. These wires are unsuitable as titanium fixation wires for the living body. They have the danger of being broken during or after the surgical operation or producing inadequatebinding.

The titanium fixation wires for the living body according to this invention described in Example 4 are intended for binding of bones and artificial bones in the human body. They have sufficient ductility (elongation) to be wound around an object to be fixed and twisted up to the binding end of the object. They permit easy and firm binding during the course of surgical operation and exhibit an eminent feature of great safety in the body. They display their particularly advantageous performance in fixing grafted bones and the like too.

As will be obvious from the foregoing detailed description and examples, this invention provides titanium implantation materials for the living body which exhibit excellent corrosion resistance in the body. More particularly, this invention provides implantation materials having adequate strength as bone replacements and reinforcements, excellent biocompatibility and corrosion resistance in vivo, and ability to enhance the connective strength with bone tissues, and hence useful in the fields of dentistry, orthopedic surgery, and the like.

The invention also provides outstanding titanium fixation wires, e.g. for binding of human bones which permits easy and firm binding during surgical operation, with high degrees of safety in the living body.

Titanium is known to have favorable fatigue strength, tensile strength, corrosion resistance, and biocompatibility. The present invention has now overcome major difficulties involved in the binding with titanium wires that have been problems yet to be solved in the art.

What is claimed is:

1. A titanium implant for the living body comprising a dental or orthopedic implant made of titanium having a corrosion resistant oxide film on the surface thereof and having the total amount of first ingredients selected from the group consisting of oxygen, hydrogen, nitrogen and carbon controlled to 10 to 4000 ppm, and the upper limit of second ingredients including Fe other than said first ingredients set to 100 ppm for purity to promote formation and regeneration of a corrosion-resistant film, the balance being titanium, so that said corrosion resistant oxide film may be promptly regenerated, even if destroyed, in vivo, wherein the implant has a tensile strength (TS) of 175 MPa or more and an elongation (El) of 10% or more.

2. A titanium implant for the living body comprising a dental or orthopedic implant made of titanium having a corrosion resistant oxide film on the surface thereof formed by anodizing, thermal oxidation, or molten salt oxidation and having the total amount of first ingredients selected from the group consisting of oxygen, hydrogen, nitrogen and carbon (excluding the oxygen contained in the surface oxide film) controlled to 10 to 4000 ppm, and the upper limit of second ingredients including Fe other than said first ingredients set to 100 ppm for purity to promote formation and regeneration of a corrosion-resistant film, the balance being titanium, so that said corrosion resistant oxide film may be promptly regenerated, even if destroyed, in vivo, wherein the implant has a tensile strength (TS) of 175 MPa or more and an elongation (El) of 10% or more.

3. The titanium for the living body of the claim 1 wherein the upper limits of the amounts of the first ingredients contained are 50 ppm for hydrogen, 200 ppm for nitrogen, and 400 ppm for carbon.

4. A wire for implanting in the living body comprising a titanium fixation wire in which the upper limits of the amounts of first ingredients contained therein are 300 ppm for oxygen, 50 ppm for hydrogen, 200 ppm for nitrogen, and 400 ppm for carbon, to give an elongation necessary for fixation; and in which the upper limit of the amounts of second ingredients other than said first ingredients is 100 ppm for purity, the balance being titanium, the wire having a tensile strength (TS) of 175 MPa or more, and an elongation (El) of 30% or more and an average crystal grain diameter of 2 to 150 $\mu$m.

5. A wire for implanting in the living body comprising a titanium fixation wire in which the upper limits of the amounts of first ingredients contained therein are 200 ppm for oxygen, 50 ppm for hydrogen, 200 ppm for nitrogen, and 400 ppm for carbon, to give an elongation necessary for fixation; and in which the upper limit of the amounts of second ingredients other than said first ingredients is 100 ppm for purity, the balance being titanium, the wire having a tensile strength (TS) of 175 MPa or more, and an elongation (El) of 30% or more and an average crystal grain diameter of 2 to 150 $\mu$m.

6. A wire for implanting in the living body comprising a titanium fixation wire in which the upper limits of the amounts of first ingredients contained therein are 100 ppm for oxygen, 50 ppm for hydrogen, 200 ppm for nitrogen, and 400 ppm for carbon, to give an elongation necessary for fixation; and in which the upper limit of the amounts of second ingredients other than said first ingredients is 100 ppm for purity, the balance being titanium, the wire having a tensile strength (TS) of 175 MPa or more, and an elongation (El) of 30% or more and an average crystal grain diameter of 2 to 150 $\mu$m.

7. The titanium fixation wire for implanting in the living body of claim 4 wherein the upper limit of the hydrogen content is 30 ppm.

8. The titanium fixation wire for implanting in the living body of claim 4 wherein the upper limit of the hydrogen content is 20 ppm.

9. The titanium fixation wire for implanting in the living body of claim 4 wherein the upper limit of the nitrogen content is 100 ppm.

10. The titanium fixation wire for implanting in the living body of claim 4 wherein the upper limit of the nitrogen content is 50 ppm.

11. The titanium fixation wire for implanting in the living body of claim 4 wherein the upper limit of the nitrogen content is 20 ppm.

12. The titanium fixation wire for implanting in the living body of claim 4 wherein the upper limit of the carbon content is 200 ppm.

13. The titanium fixation wire for implanting in the living body of claim 4 wherein the upper limit of the carbon content is 100 ppm.

14. The titanium fixation wire for implanting in the living body of claim 4 wherein the upper limit of the carbon content is 50 ppm.

15. The titanium fixation wire for implanting in the living body of any of the claims 4 to 6 wherein the upper limit of the amounts of said second ingredients other than said first ingredients is 50 ppm.

16. The titanium fixation wire for implanting in the living body of any of the claims 4 to 6 wherein the upper limit of the amounts of said second ingredients other than said first ingredients is 20 ppm.

17. A wire for implanting in the living body comprising a titanium fixation wire in which the upper limits of the amounts of first ingredients contained therein are 100 ppm for oxygen, 30 ppm for hydrogen, 100 ppm for nitrogen, and 200 ppm for carbon, to give an elongation necessary for fixation; and in which the upper limit of the amounts of second ingredients other than said first ingredients is 50 ppm for purity, the balance being titanium, the wire having a tensile strength (TS) of 175 MPa or more, and an elongation (El) of 30% or more and an average crystal grain diameter of 2 to 150 $\mu$m.

18. A wire for implanting in the living body comprising a titanium fixation wire in which the iron content is from 100 to 1000 ppm so as to enhance strength; the upper limits of the amounts of first ingredients contained are 250 ppm for oxygen, 50 ppm for hydrogen, 170 ppm for nitrogen, and 340 ppm for carbon; and in which the upper limit of the amounts of second ingredients other than iron and said first ingredients is 100 ppm, the balance being titanium, the wire having a tensile strength (TS) of 175 MPa or more and an elongation (El) of 30% or more.

19. A wire for implanting in the living body comprising a titanium fixation wire in which the iron content is from 100 to 800 ppm so as to enhance strength; the upper limits of the amounts of first ingredients contained are 250 ppm for oxygen, 50 ppm for hydrogen, 170 ppm for nitrogen, and 340 ppm for carbon; and in which the upper limit of the amounts of second ingredients other than iron and said first ingredients is 100 ppm, the balance being titanium, the wire having a tensile strength (TS) of 175 MPa or more and an elongation (El) of 30% or more.

20. A wire for implanting in the living body comprising a titanium fixation wire in which the iron content is from 100 to 600 ppm so as to enhance strength; the upper limits of the amounts of first ingredients contained are 250 ppm for oxygen, 50 ppm for hydrogen, 170 ppm for nitrogen, and 340 ppm for carbon; and in which the upper limit of the amounts of second ingredients other than iron and said first ingredients is 100 ppm, the balance being titanium, the wire having a tensile strength (TS) of 175 MPa or more and an elongation (El) of 30% or more.

21. The titanium fixation wire for implanting in the living body of claim 18 wherein the upper limit of the oxygen content is 200 ppm.

22. The titanium fixation wire for implanting in the living body of claim 18 wherein the upper limit of the oxygen content is 150 ppm.

23. The titanium fixation wire for implanting in the living body of claim 18 wherein the upper limit of the hydrogen content is 30 ppm.

24. The titanium fixation wire for implanting in the living body of claim 18 wherein the upper limit of the hydrogen content is 20 ppm.

25. The titanium fixation wire for implanting in the living body of claim 18 wherein the upper limit of the nitrogen content is 100 ppm.

26. The titanium fixation wire for implanting in the living body of claim 18 wherein the upper limit of the nitrogen content is 50 ppm.

27. The titanium fixation wire for implanting in the living body of claim 18 wherein the upper limit of the nitrogen content is 20 ppm.

28. The titanium fixation wire for implanting in the living body of claim 18 wherein the upper limit of the carbon content is 200 ppm.

29. The titanium fixation wire for implanting in the living body of claim 18 wherein the upper limit of the carbon content is 100 ppm.

30. The titanium fixation wire for implanting in the living body of claim 18 wherein the upper limit of the carbon content is 50 ppm.

31. The titanium fixation wire for implanting in the living body of claim 18 wherein the upper limit of the amounts of said second ingredients other than iron and said first ingredients is 50 ppm.

32. The titanium fixation wire for implanting in the living body of claim 18 wherein the upper limit of the amounts of said second ingredients other than iron and said first ingredients is 20 ppm.

33. A wire for implanting in the living body comprising a titanium fixation wire in which the iron content is from 100 to 600 ppm so as to enhance strength; the upper limits of the amounts of first ingredients contained are 200 ppm for oxygen, 30 ppm for hydrogen, 100 ppm for nitrogen, and 200 ppm for carbon; and in which the upper limit of the amounts of second ingredients other than iron and said first ingredients is 100 ppm, the balance being titanium, the wire having a tensile strength (TS) of 175 MPa or more and an elongation (El) of 30% or more.

34. The titanium fixation wire for implanting in the living body of claim 18 wherein the average crystal grain diameter of the wire is 2 to 150 $\mu$m.

35. The titanium fixation wire for implanting in the living body of the claims 33 wherein the average crystal grain diameter of the wire is 2 to 150 $\mu$m.

36. The titanium fixation wire for implanting in the living body of claim 4 wherein the lower limit of oxygen content is 10 ppm.

37. The titanium fixation wire for implanting in the living body of claim 18 wherein the lower limit of oxygen content is 10 ppm.

* * * * *